United States Patent [19]

Antoine et al.

[11] Patent Number: 5,053,509

[45] Date of Patent: Oct. 1, 1991

[54] BENZO(1,8)NAPHTHYRIDINE DERIVATIVES, THEIR PREPARATION AND COMPOSITIONS CONTAINING THEM

[75] Inventors: Michel Antoine, Paris; Michel Barreau, Montgeron; Jean-Francois Desconclois, Paris; Philippe Girard, Arpajon; Guy Picaut, Villejuif, all of France

[73] Assignee: Laboratoire Roger Bellon, Seine, France

[21] Appl. No.: 605,340

[22] Filed: Oct. 30, 1990

[30] Foreign Application Priority Data

Oct. 30, 1989 [FR] France .................................. 89 14203
Jul. 10, 1990 [FR] France .................................. 90 08757

[51] Int. Cl.$^5$ ................... A61K 31/495; C07D 471/06
[52] U.S. Cl. ..................................................... 544/361
[58] Field of Search ......................... 544/361; 514/254

[56] References Cited

U.S. PATENT DOCUMENTS 4,133,885  1/1979  Bolhofer et al. ..................... 546/113

OTHER PUBLICATIONS

Schrorrenberg et al., CA 102–24611a (1985).
Antoine et al., CA 114–62083k (1991).
Antoine et al., CA 114–62082j (1991).

Primary Examiner—Cecilia Shen

Attorney, Agent, or Firm—Morgan & Finnegan

[57] ABSTRACT

New bonzo[b][1,8]naphthyridine derivatives of general formula (I), in which $R_1$ is a hydrogen atom or a hydroxyl or alkyl radical, $R_2$ is a hydrogen atom or an alkyl, fluoroalkyl, cycloalkyl (3 to 6 C), alkyloxy or alkylamino radical, $R_3$ is a phenyl or phenylalkyl radical substituted with one or more halogen atoms or alkyl, cycloalkyl (3 to 6 C), alkyloxy, cyano, amino, alkylamino, dialkylamino, alkyloxyalkyl, hydroxyalkyl, hydroxyalkyloxy, methylenedioxy, aminoalkyl, alkylaminoalkyl or dialkylaminoalkyl radicals, or $R_3$ is a heterocyclic radical, and $R_4$ is a hydrogen atom or a fluorine atom, the alkyl radicals (1 to 4 C) being linear or branched, their salts, their preparation and compositions containing them.

These new products are useful as antimicrobials, or in the treatment of AIDS.

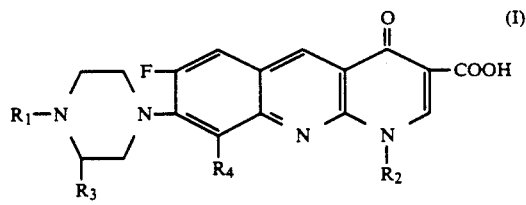

7 Claims, No Drawings

BENZO(1,8)NAPHTHYRIDINE DERIVATIVES, THEIR PREPARATION AND COMPOSITIONS CONTAINING THEM

FIELD OF THE INVENTION

The present invention relates to new benzo[b][1,8]naphthyridine derivatives of general formula:

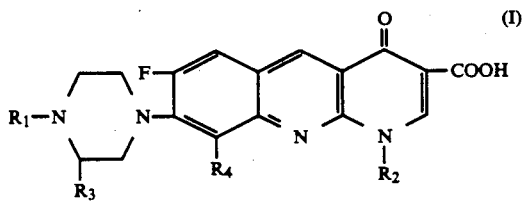

to their salts, to their preparation and to compositions containing them.

BACKGROUND OF THE INVENTION

In U.S. Pat. Nos. 4,229,456 and 4,133,885, naphthyridine derivatives of structure:

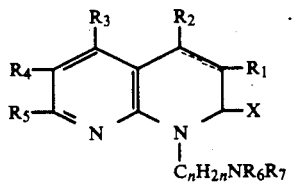

in which X can be oxygen and two of the adjacent radicals $R_1$ to $R_5$ can form a benzene ring, have been described.

These products are useful as inhibitors of acidic gastric secretions.

Patent application DE 3,302,126 describes hypotensives of general formula:

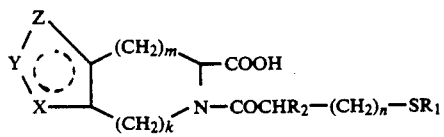

in which the radicals X, Y and Z can be O or a radical $NR_4$ or $CR_5=CR_5$, in which the groups $R_5$ can form a benzene ring.

DETAILED DESCRIPTION OF THE INVENTION

It has been found that the products of general formula (I) in which:

$R_1$ represents a hydrogen atom or a hydroxyl or alkyl radical, $R_2$ represents a hydrogen atom or an alkyl or fluoroalkyl radical, a cycloalkyl radical containing 3 to 6 carbon atoms or alkyloxy or alkylamino radical, $R_3$ represents a phenyl or phenylalkyl radical optionally substituted with one or more halogen atoms or alkyl radicals, cycloalkyl radicals containing 3 to 6 carbon atoms, alkyloxy, cyano, amino, alkylamino, dialkylamino, alkyloxyalkyl, hydroxyalkyl, hydroxyalkyloxy, methylenedioxy, aminoalkyl or alkylaminoalkyl radicals or dialkylaminoalkyl radicals in which the alkyl portions, with the nitrogen atom to which they are attached, can form a 5- or 6-membered heterocycle, or represents a 5-membered heterocyclic radical containing 1 or 2 hetero atoms selected from nitrogen, oxygen or sulphur, and $R_4$ represents a hydrogen atom or a fluorine atom, and in which the alkyl radicals are linear or branched and contain 1 to 4 carbon atoms, as well as their salts and their isomers, manifest an especially advantageous antibacterial activity.

The products of general formula (I) can exist in the state of a hydrated form; it is understood that these hydrates also fall within the scope of the present invention.

In the general formula (I), when $R_3$ represents a heterocyclic radical, the latter can advantageously be selected from furyl, thienyl, pyrrolyl, N-alkylpyrrolyl, imidazolyl, pyrazolyl or thiazolyl.

According to the invention, the products of general formula (I) may be obtained by the substitution of a piperazine of general formula:

in which $R_1$ and $R_3$ are defined as above, on a benzo[b][1,8]naphthyridine of general formula:

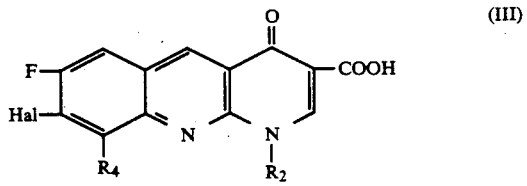

in which $R_2$ is defined as above, Hal is a fluorine, chlorine or bromine atom if $R_4$ is hydrogen, or alternatively Hal and $R_4$ are simultaneously fluorine atoms, followed, where appropriate, if $R_1$ is a hydrogen atom and if it is desired to obtain a benzo[b][1,8]naphthyridine derivative in which $R_1$ is methyl, by conversion of the product obtained to an 8-(4-methyl-1-piperazinyl)-benzo[b]naphthyridine.

The action of the piperazine derivative of general formula (II) is generally performed in the presence of an excess of this derivative as an acceptor for acid in suitable organic solvents. It is possible to work with or without a solvent, at a temperature of between 30° and 120° C. When the reaction is carried out in the presence of a solvent, it is advantageously performed in solvents such as pyridine, dimethylformamide, dimethyl sulphoxide or acetonitrile.

It can also be advantageous to work in the presence of an acceptor for acid such as, e.g., a nitrogenous organic base (triethylamine in particular), an alkali metal carbonate (e.g. sodium carbonate) or an alkali metal hydroxide or alkaline earth metal hydroxide.

It is understood that, in the case where the symbol $R_2$ in the product of general formula (III) is a hydrogen atom, or when $R_3$ contains an amino, alkylamino, aminoalkyl or alkylaminoalkyl substituent, it is preferable to protect the starting substance beforehand. The protection and removal of the protective radical after the reaction is performed according to the usual methods.

The protection may be carried out with any compatible group whose use and removal do not adversely affect the remainder of the molecule. In particular, the protection is performed according to the methods described by T. W. GREENE, Protective Groups in Organic Synthesis, A. Wiley-Interscience Publication (1981), or by McOMIE, Protective Groups in Organic Chemistry, Plenum Press (1973).

By way of example, the protective groups may be selected from trimethylsilyl, benzhydryl, tetrahydropyranyl, formyl, acetyl, chloroacetyl, trichloroacetyl, trifluoroacetyl, ethoxycarbonyl, t-butoxycarbonyl and trichloroethoxycarbonyl radicals.

Where appropriate, the subsequent operation of methylation of the piperazinyl radical is advantageously performed by the action of formaldehyde in the presence of formic acid. The reaction is generally performed in an aqueous medium, at a temperature of between 90° and 100° C.

According to the invention, the benzo[b][1,8]naphthyridine derivatives of general formula (I) may also be obtained from the corresponding ester of general formula:

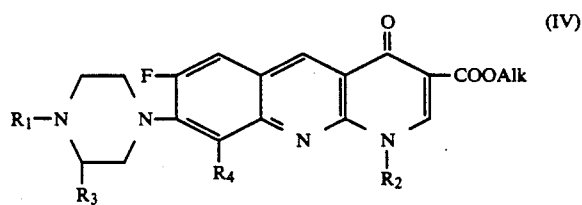
(IV)

in which $R_1$, $R_3$ and $R_4$ are defined as above, $R_2$ is defined as above or represents a protected alkylamino radical and Alk represents an alkyl radical containing 1 to 4 carbon atoms in a straight or branched chain, by any known method for obtaining an acid from an ester without affecting the remainder of the molecule, followed, where appropriate, by removal of the group protecting the alkylamino radical and/or, if a product of general formula (I) in which $R_1$ is a hydrogen atom has been obtained and if it is desired to obtain the corresponding product for which $R_1$ is methyl, followed by conversion of the product obtained to an 8-(4-methyl-1-piperazinyl)benzo[b]naphthyridine.

The preparation of the acid from the ester is generally performed by acid hydrolysis. It is advantageous to work in an acetic acid/hydrochloric acid mixture, in sulphuric acid or in methanesulphonic acid at a temperature of between 20° and 100° C. It is also possible to perform a reaction by saponification in the presence of potassium hydroxide or sodium hydroxide, in an aqueous-alcoholic medium, at a temperature of between 20° and 80° C.

Where appropriate, the methylation of the piperazinyl radical is performed as described above.

When $R_2$ represents a protected alkylamino radical, the protective radical can be any amino-protecting group compatible with the molecule. It is especially advantageous to select a protective radical which can be removed simultaneously with the hydrolysis of the ester.

The benzo[b][1,8]naphthyridine derivative of general formula (III) may be obtained from the corresponding ester of general formula:

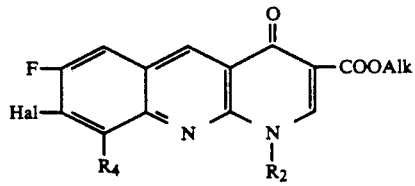
(V)

in which $R_4$, Hal and Alk are defined as above and $R_2$ is defined as above or represents a protected alkylamino radical, by any known method for obtaining an acid from an ester without affecting the remainder of the molecule, followed, where appropriate, by removal of the group protecting the alkylamino radical.

The reaction is performed, in particular, under the conditions described above for obtaining a product of general formula (I) from an ester of general formula (IV).

The ester derived from the benzo[b][1,8]naphthyridine of general formula (V) may be prepared by the action of 3-amino-1,2,4-triazine to obtain a product for which $R_2$ is a hydrogen atom, or by the action of a product of general formula:

$$R_2-NH_2 \qquad (VI)$$

in which $R_2$ is alkyl, fluoroalkyl, cycloalkyl, alkyloxy or alkylamino, protected where appropriate, on a quinoline derivative of general formula:

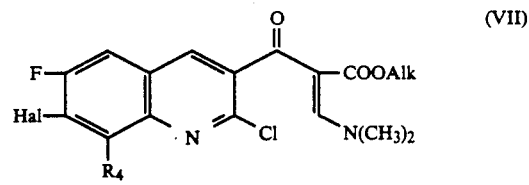
(VII)

in which $R_4$, Hal and Alk are defined as above, followed by cyclization by the action of an acceptor for acid.

In general, the reaction of 3-amino-1,2,4-triazine or of the product of general formula (VI) is carried out in an organic solvent such as an alcohol (e.g. ethanol, methanol) or a chlorinated solvent (e.g. trichloromethane), at a temperature of between 10° and 25° C.

The cyclization is performed in a straight-or branched-chain alcohol containing 1 to 4 carbon atoms, at a temperature of between 20° C. and the refluxing temperature of the reaction mixture.

The acceptor for acid can be, in particular, selected from nitrogenous bases (e.g. triethylamine), 1,8-diazabicyclo[5.4.0]undec-7-ene or an excess of the amine employed.

The quinoline derivative of general formula (VII) may be obtained from the keto ester of general formula:

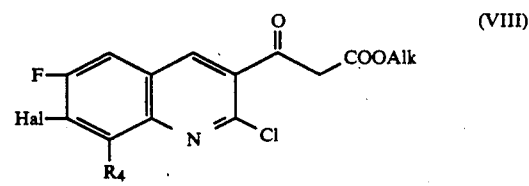
(VIII)

in which R4, Hal and Alk are defined as above, by the action of an N,N-dimethylformamide acetal of general formula:

$$(CH_3)_2N-CH(OAlk_1)_2 \quad (IX)$$

in which Alk₁ is an alkyl radical containing 1 to 4 carbon atoms in a straight or branched chain.

The reaction is generally performed in a organic solvent such as an ester (e.g. ethyl acetate) at a temperature of between 60° and 75° C.

The keto ester of general formula (VIII) for which R4 is a hydrogen atom and Hal is defined as above may be obtained from 2,7-dichloro-6-fluoro-3-quinolinecarboxylic acid or 2-chloro-6,7-difluoro-3-quinolinecarboxylic acid as described below in Example 1, or from 7-bromo-2-chloro-6-fluoro-3-quinolinecarboxylic acid by a procedure analogous to this method. In this case, 3-bromo-4-fluoroaniline, used as a starting substance, may be prepared according to the method described by W. B. Austin et al, J. Org. Chem., 46(11), 2280 (1981).

The keto ester of general formula (VIII) for which R4 and Hal are simultaneously fluorine atoms may be obtained from 2-chloro-6,7,8-trifluoro-3-quinolinecarboxylic acid as described below in Example 25.

The benzo[b][1,8]naphthyridine derivative of general formula (IV) may be obtained from the benzo[b]naphthyridine of general formula (V) by the substitution of a piperazine derivative of general formula (II).

When R3 represents a phenyl radical substituted with amino, the benzo[b]naphthyridine derivative of general formula (IV) may also be obtained by reduction of the corresponding nitro derivative, as described below in Example 35.

It is advantageous to work under the conditions described above to obtain a product of general formula (I) from a piperazine of general formula (II) and a benzo[b][1,8]naphthyridine of general formula (III).

The piperazine of general formula (II) may be obtained by application of the methods described by:
E. Jucker et al, Helv. Chim. Acta, 45(7), 2383 (1962);
European Patent Application 230,053;
Patent Application FR 2,351,108;
Japanese Patent Application 01 117 869;
Toschio Uno et al., J. Het. Chem., 26 393 (1988);
W. R. Roderick et al., J. Med. Chem., 9, 181 (1966);
J. D. Behan et al., J. Org. Chem, 26, 3379 (1961);
J. W. H. Watthey et al., J. Med. Chem., 26, 1116 (1983);
L. J. Kitchen et al., J. Am. Chem. Soc., 69, 854 (1947) and J. Org. Chem., 8, 342 (1943);
J. D. Behun et al., J. Org. Chem., 26, 3379 (1961)
or by application of, or procedures analogous to, the methods described below in the examples. It is understood that it is sometimes necessary to perform chromatography of the piperazine obtained.

The piperazines of general formula (II) for which R₁ is a hydroxyl radical and R3 is other than a hydrogen atom may be prepared by oxidation of the corresponding piperazine in which the nitrogen atom at the 4-position has been protected beforehand, according to the method described by A.J. Biloski et al., Synthesis, 537 (1983).

When R3 represents a phenyl radical substituted with a dialkylaminomethyl radical, the piperazine of general formula (II) may be obtained from a 2-(hydroxyphenyl)piperazine in which the nitrogen atoms have been protected beforehand with any compatible group, by application of the method described by M. Tromontini, Synthesis, 703-775 (1973).

According to the invention, when it is desired to obtain the isomers of the benzonaphthyridine derivatives of general formula (I), the separation of the isomeric forms of the piperazines of general formula (II) is performed by any known method compatible with the molecule. By way of example, the separation is performed by acylation by means of a chiral acid or a reactive derivative of a chiral acid, separation of the isomers by high performance liquid chromatography and then deacylation by acid hydrolysis.

In the examples which follow, (−) isomer denotes the (S) isomer of the benzonaphthyridine derivative of general formula (I), the optical rotation of which in solution in acetic acid is negative, obtained from the piperazine derivative the optical rotation of which in ethanol is positive; (+) isomer denotes the (R) isomer of the benzonaphthyridine derivative of general formula (I), the optical rotation of which in solution in acetic acid is positive, obtained from the piperazine derivative the optical rotation of which in solution in ethanol is negative.

It is also possible to perform the synthesis of the chiral piperazine directly, as described below in Examples 20 and 21.

The new products according to the present invention, as well as their synthesis intermediates, may be purified, where appropriate, by physical methods such as crystallization or chromatography.

The products according to the invention may be converted to metal salts or to addition salts with nitrogenous bases according to methods known per se. These salts may be obtained by the action of a metallic (e.g. alkali metal or alkaline earth metal) base, ammonia or an amine on a product according to the invention in a suitable solvent such as an alcohol, an ether or water, or by an exchange reaction with a salt of an organic acid. The salt formed precipitates after concentration,, where appropriate, of the solution, and is separated by filtration, decantation or lyophilization.

The new products according to the invention may also be converted to addition salts with acids. The products of general formula (I) obtained in the form of these salts may be liberated and converted to salts of other acids according to the usual methods.

As examples of pharmaceutically acceptable salts, the salts with alkali metals (sodium, potassium, lithium) or with alkaline earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine) and also the addition salts with inorganic acids (hydrochlorides, hydrobromides, sulphates, nitrates, phosphates) or organic acids (succinates, fumarates, maleates, methanesulphonates, p-toluenesulphonates, isethionates) may be mentioned.

The new benzo[b][1,8]naphthyridine derivatives of general formula (I) according to the present invention and their pharmaceutically acceptable salts posses especially advantageous antibacterial properties. They manifest an exceptional in vitro and in vivo activity against gram-positive microorganisms and, generally speaking, against the microorganisms responsible for most of the infections of the upper and lower airways.

In vitro, the products of general formula (I) have been shown to be active at a concentration of between 0.12 and 4 μg/cc against Staphylococcus aureus IP 8203.

In vivo, the products of general formula (I) have been shown to be active against experimental Staphylococcus aureus IP 82-3 infections in mice, at subcutaneous doses of between 2 and 200 mg/kg or at oral doses of between 4 and 150 mg/kg.

Another advantage of the products according to the invention is their low toxicity. Their subcutaneous $LD_{50}$ is generally greater than 500 mg/kg in mice.

Moreover, the products according to the invention have proved especially advantageous for the prophylaxis and treatment of AIDS (acquired immune deficiency syndrome) and associated syndromes [ARC (AIDS-related complex)].

The test products inhibit the cytopathogenic effect of the HIV virus in cell culture at concentrations devoid of a cytotoxic or cytostatic effect.

Activity with respect to the cytopathogenic effect of the HIV virus.

The powdered products were dissolved in the proportion of 2 mg of product per ml (approximately $4 \times 10^{-3}$ M) in a mixture of dimethyl sulphoxide (DMSO) and L-lysine (base) (1:19, vol/vol). DMSO (1 volume) is added first and the product is solubilized as far as possible, then a solution (19 volumes) of L-lysine base at a concentration of $4 \times 10^{-3}$ M in distilled water is added. The mixture is then maintained for 15 minutes at 60° C. In this way, a stock solution of product incorporating DMSO (5%) and containing a (product/lysine) mole ratio in the vicinity of 1 is obtained. The test is carried out on lymphoblastoid line CEM clone 13. A solution (25 μl/well) of test product in isotonic phosphate buffer (IPB), or IPB alone in the case of the controls, is deposited in a 96-well microplate. The products are studied at different concentrations (often 8), on the basis of 6 wells per concentration. A suspension (125 μl) of CEM cells (between 5 and $8 \times 10^4$ cells per ml) in RPMI medium containing fetal calf serum (10%), penicillin (100 IU/ml), streptomycin (100 μg/ml), and glutamine (2 μmol/ml) is then added and the microplates are incubated for one hour at 37° C. under an atmosphere containing 5% of carbon dioxide. For each concentration, the test is divided into two parts: one part (3 wells) on infected cells for determination of the antiviral activity, and the other part (3 wells) on uninfected cells to determine the cytotoxicity of the products. The first series is then infected with HIV-1 (100 μl per well of a suspension of LAV-1-BRU virus containing 200–300 $TCID_{50}$), while the other series receives RPMI medium (100 μl) as defined above. After 7 days' incubation, cells (150 μl) are removed to measure cell viability [determined according to a modification of the technique described by R. Pauwels et al., J. Virol. Meth., 20, 309–321 (1988)]. To this sample, a solution (10 μl) containing MTT [(4,5-dimethyl-2-thiazolyl)-2,5-diphenyltetrazolium bromide] (7 mg per ml of isotonic phosphate buffer is added. After 3 hours' incubation at 37° C., the supernatant is removed. The MTT is converted to a (blue) formazan salt inside the living cells and in proportion to their number, whereas nothing is seen in the wells now containing only dead cells. Isopropanol (containing 0.04 mol/l of hydrochloric acid) (100 's then added and the microplates are agitated until the formazan blue has been solubilized. The absorbance at 540 nm is read with an automatic reader for microplate ELISA reactions. This absorbance is proportional to the number of living cells. The results obtained at day 14 are given in Table I below.

TABLE I

| Test product | Concentration of the test product μg/ml | Results at D14 Optical Density (OD) | | % protection |
|---|---|---|---|---|
| | | infected cells | uninfected cells | |
| Example 1 | 0 | 321 | 1151 | 0% |
| | 0.014 | 300 | 1285 | −2% |
| | 0.04 | 285 | 1310 | −4% |
| | 0.12 | 335 | 1285 | 1% |
| | 0.37 | 425 | 1188 | 12% |
| | 1.11 | 842 | 1010 | 76% |
| | 3.33 | 747 | 867 | 78% |
| | 10 | 850 | 844 | 101% |
| Example 21 | 0 | 489 | 1227 | 0% |
| | 0.014 | 543 | 1196 | 8% |
| | 0.04 | 1086 | 1228 | 81% |
| | 0.12 | 1104 | 1162 | 91% |
| | 0.37 | 1132 | 1145 | 98% |
| | 1.11 | 945 | 1021 | 86% |

The degree of protection (in %) of a given product is determined by the formula:

$$\frac{OD(\text{cells treated and inf.}) - OD(\text{cells not treated and inf.})}{OD(\text{cells treated and not inf.}) - OD(\text{cells not treated and inf.})}$$

Especially advantageous are the products of the general formula (I) in which:

$R_1$ represents a hydrogen atom or a hydroxyl or alkyl radical, $R_2$ represents a hydrogen atom or an alkyl or fluoroalkyl radical, a cycloalkyl radical containing 3 to 6 carbon atoms or an alkyloxy radical, $R_3$ represents a phenyl or phenylalkyl radical optionally substituted with one or more halogen atoms or alkyl radicals, cycloalkyl radicals containing 3 to 6 carbon atoms or alkyloxy, cyano, amino, alkyloxyalkyl, hydroxyalkyloxy or methylenedioxy radicals, or represents a 5-membered heterocyclic radical containing 1 or 2 hetero atoms selected from nitrogen, oxygen or sulphur, and $R_4$ represents a hydrogen atom or a fluorine atom.

Among these products, the following benzonaphthyridine derivatives are more especially advantageous:

7-fluoro-1-methyl-4-oxo-8-(3-phenyl-1-piperazinyl)-1,4-dihydrobenzo[b][1,8]naphthyridine-3-carboxylic acid in its isomeric forms and mixtures thereof;

7-fluoro-1-methyl-8-[3-(4-methylphenyl)-1-piperazinyl]-4-oxo-1,4-dihydrobenzo[b][1,8]-naphthyridine-3-carboxylic acid in its isomeric forms and mixtures thereof;

7-fluoro-8-[3-(4-methoxyphenyl)-1-piperazinyl]-1-methyl-4-oxo-1,4-dihydrobenzo[b][1,8]naphthyridine-3-carboxylic acid in its isomeric forms and mixtures thereof;

7,9-difluoro-8-[3-(4-methoxyphenyl)-1-piperazinyl]-1-methyl-4-oxo-1,4-dihydrobenzo[b][1,8]naphthyridine-3-carboxylic acid in its isomeric forms and mixtures thereof; and 7-fluoro-8-[3-(2-furyl)-1-piperazinyl]-1-methyl-4-oxo-1,4-dihydrobenzo[b][1,8]naphthyridine-3-carboxylic acid in its isomeric forms and mixtures thereof.

EXAMPLES

The examples which follow, given without implied limitation, illustrate the present invention.

EXAMPLE 1

A suspension of 8-chloro-7-fluoro-1-methyl-4-oxo-1,4-dihydrobenzo[b][1,8]naphthyridine-3-carboxylic acid (1.84 g) in pyridine (20 cc), (RS)-2-phenylpiperazine (5.83 g) and triethylamine (1.24 g) is heated to a temperature in the region of 115° C. for 5 hours. After cooling to approximately 20° C., the precipitate formed is drained and washed with pyridine (2×5 cc), isopropyl alcohol (2×5 cc), ethanol (2×5 cc) and ethyl ether (1×20 cc). After 1 recrystallization in a mixture of dimethylformamide (40 cc) and ethanol (40 cc), (RS)-7-fluoro-1-methyl-4-oxo-8-(3-phenyl-1-piperazinyl)-1,4-dihydrobenzo[b][1,8]naphthyridine-3-carboxylic acid (0.920 g) is obtained in the form of a yellow solid, m.p. 265° C.

8-Chloro-7-fluoro-1-methyl-4-oxo-1,4-dihydrobenzo[b][1,8]naphthyridine-3-carboxylic acid may be prepared in the following manner:

A suspension of 8-chloro-3-ethoxycarbonyl-7-fluoro-1-methyl-4-oxo-1,4-dihydrobenzo[b][1,8]-naphthyridine (15 g) in acetic acid (150 cc) and 17.5% strength aqueous hydrochloric acid solution (150 cc) is heated to a temperature in the region of 100° C. with stirring for 4 hours. After cooling to a temperature in the region of 20° C., the product is drained, washed with water (2×100 cc) and washed with ethanol (2×150 cc) and then ethyl ether (2×100 cc). 8-Chloro-7-fluoro-1-methyl-4-oxo-1,4-dihydrobenzo[b][1,8]naphthyridine-3-carboxylic acid (12.7 g) is obtained in the form of a beige solid, subliming at 400°–405° C., which is used without further purification for the subsequent steps.

8-Chloro-3-ethoxycarbonyl-7-fluoro-1-methyl-4-oxo-1,4-dihydrobenzo[b][1,8]naphthyridine is prepared in the following manner:

Methylamine is bubbled into a stirred suspension, maintained at between 10° and 15° C., of ethyl 2-(2,7-dichloro-6-fluoro-3-quinolinecarbonyl)-3-(dimethylamino)acrylate (19.3 g) in ethanol (250 cc) until 16 g of gas have been absorbed. The temperature is allowed to rise to approximately 20 C., 1,8-diazabicyclo[5.4.0]undec-7-ene (DBU) (0.8 g) is added and the mixture is heated to a temperature in the region of 75° C. for 2 hours. After cooling to approximately 20° C., the product is drained and washed with ethanol (2×150 cc) and ethyl ether (2×100 cc). 8-Chloro-3-ethoxycarbonyl-7-fluoro-1-methyl-4-oxo-1,4-dihydrobenzo[b][1,8]naphthyridine (15 g) is obtained in the form of a yellow solid, m.p. 360°–362° C., which is used without further purification for the subsequent steps.

Ethyl 2-(2,7-dichloro-6-fluoro-3-quinolinecarbonyl)-3-(dimethylamino)acrylate is prepared in the following manner:

A suspension of ethyl 3-(2,7-dichloro-6-fluoro-3-quinolinyl)-3-oxopropionate (16.5 g) in ethyl acetate (160 cc) and N,N-dimethylformamide dimethyl acetal (19 cc) is heated to a temperature in the region of 75° C. with stirring for 2 hours. The reaction mixture is concentrated to dryness under reduced pressure (20 kPa) at 50° C. The dry extract is taken up with isopropyl ether (50 cc), drained and washed with isopropyl ether (2×10 cc). Ethyl 2-(2,7-dichloro-6-fluoro-3-quinolinecarbonyl)-3-(dimethylamino)acrylate (16.57 g) is obtained in the form of an orange-colored solid, m.p. 122° C. This product is used without further purification for the subsequent steps.

Ethyl 3-(2,7-dichloro-6-fluoro-3-quinolyl)-3-oxopropionate is prepared in the following manner:

A suspension of 2,7-dichloro-6-fluoro-3-quinolinecarboxylic acid (38.75 g) in trichloromethane (410 cc) and thionyl chloride (24 cc) is heated to a temperature in the region of 60° C. with stirring for 6 hours. The solution obtained is concentrated to dryness under reduced pressure (20 kPa) at 50° C. The dry extract is taken up twice with toluene (200 cc in total) and concentrated again under reduced pressure under the same conditions as above. The yellow solid obtained (m.p. 124° C.), is dissolved in anhydrous tetrahydrofuran (230 cc). The solution obtained is introduced dropwise, with stirring, in the course of 30 minutes and at between 5° and 10° C. into a solution (200 cc) of magnesium chelate in tetrahydrofuran. The temperature is allowed to rise to 20° C. and the mixture is stirred for 1 and a half hours at this temperature. The solution obtained is introduced dropwise, with stirring and at a temperature in the region of 5° C. into 0.5 N sulphuric acid (1 liter). The temperature of the suspension obtained is allowed to rise to 20° C. and the mixture is stirred for a further 2 hours at this temperature. The product is extracted with ethyl acetate (1 liter), the organic and aqueous phases are filtered through diatomaceous silica for filtration which enables some slight insoluble matter to be removed and the aqueous phase is extracted twice more with ethyl acetate (500 cc). The combined organic extracts are washed with water (2×500 cc), dried over magnesium sulphate, filtered and concentrated to dryness under reduced pressure (20 kPa) at 40° C. The residue is taken up with isopropyl ether (100 cc) at 20° C., drained and washed with isopropyl ether (2×30 cc). Ethyl 3-(2,7-dichloro-6-fluoro-3-quinolyl)-3-oxopropionate (40.55 g) is obtained in the form of a beige solid, m.p. 112°–114° C. This product is used without further purification for the subsequent steps.

Preparation of the magnesium chelate of ethyl monomalonate:

Absolute ethanol (5 cc), tetrachloromethane (0.2 cc) and ethyl monomalonate (2 g) are added gradually to magnesium turnings (6.9 g). After heating, a solution of ethyl monomalonate (23.8 g) in ethanol (450 cc) is added in the course of 15 minutes. The mixture is heated for 20 hours to a temperature in the region of 78° C. and concentrated under reduced pressure (20 kPa) at 50° C. The residue is taken up with toluene (2×100 cc) and concentrated under reduced pressure under the same conditions as above. The grey powder obtained is dissolved by adding anhydrous tetrahydrofuran so as to obtain a total volume of 200 cc.

Ethyl monomalonate was prepared according to the method described by D. S. Breslow, E. Baumgarten, C. R. Hauser, J. Am. Chem. Soc., 66, 1287 (1944) and distilled under reduced pressure (boiling point=132° C./2.7 kPa).

2,7-Dichloro-6-fluoroquinoline-3-carboxylic acid is prepared in the following manner:

A solution of potassium permanganate (89.3 g) in water (1.4 liters) is added in the course of 1 hour to a stirred suspension, cooled to 10° C., of 2,7-dichloro-6-fluoro-3-formyl-1,4-dihydroquinoline (69.5 g) in 2 N aqueous potassium hydroxide (282 cc) and water (282 cc) while the temperature is maintained at between 10° and 14° C. The temperature is allowed to rise to approximately 20° C. and the mixture is stirred for a further 30 minutes at this temperature. Sodium dithionite (26 g) is added and the mixture is stirred for 10 minutes at a temperature in the region of 20° C., filtered through diatomaceous silica for filtration and washed with water (2×250 cc). The filtrate and the aqueous washing phases are combined and treated with 35% strength aqueous hydrochloric acid solution (90 cc). The precipitate formed is extracted with ethyl acetate (4×500 cc). The combined organic extracts are washed with water (3×500 cc), dried over magnesium sulphate, filtered and concentrated under reduced pressure (20 kPa) at 50° C. The residue is taken up with ethyl ether (350 cc), drained and washed with ethyl ether (2×200 cc). 2,7-Dichloro-6-fluoro-3-quinolinecarboxylic acid (45 g) is obtained in the form of a beige solid, m.p. 230° C., which is used without further purification for the subsequent steps.

2,7-Dichloro-6-fluoro-3-formyl-1,4-dihydroquinoline was prepared in the following manner:

Phosphoryl chloride (55.6 cc) is added in the course of 30 minutes, with stirring at between 10° and 15° C. to a mixture of trichloromethane (250 cc) and dimethylformamide (54 cc) and the mixture is stirred for 1 hour at a temperature in the region of 20° C. To the solution obtained, 7-chloro-6-fluoro-3,4-dihydrocarbostyril (52 g) is added gradually in the course of 10 minutes at approximately 20° C. with vigorous stirring. The suspension obtained is heated to a temperature in the region of 60° C. and kept stirring for a further 2 hours at this temperature. The reaction mixture is concentrated under reduced pressure (20 kPa) at 50° C. until a pasty mixture is obtained. A mixture of water (250 cc) and crushed ice (250 g) is added with vigorous stirring. The solid obtained is drained at approximately 5° C. and washed with water (4×125 cc) at 5° C. The wet product obtained and sodium acetate (58 g) are added simultaneously in the course of 1 hour to water (500 cc) at 90° C., so as to maintain the pH at approximately 6. The mixture is stirred for a further 15 minutes at 90° C., the temperature is allowed to fall to approximately 50° C. and the product is drained at this temperature and washed with water (3×250 cc) at approximately 20° C. 2,7-Dichloro-6-fluoro-3-formyl1,4-dihydroquinoline (54.3 g) is obtained in the form of a yellow solid, m.p. 260° C., which is used without further treatment for the subsequent steps.

7-Chloro-6-fluoro-3,4-dihydrocarbostyril is prepared in the following manner:

Aluminium chloride (350 g) is added with vigorous stirring in the course of 5 minutes to 3'-chloro-4'-fluoro-3-chloropropionanilide (174.4 g). The solid mixture is heated in the course of 30 minutes to approximately 60° C. The temperature rises spontaneously to approximately 80° C. and the reaction mixture becomes liquid. The mixture is then heated to 110° C. in the course of 15 minutes and maintained at between 110 and 120° C. for 3 hours. The reaction mixture (at approximately 110° C.) is poured in the course of 10 minutes with vigorous stirring into a mixture of 35% strength hydrochloric acid (550 cc) and crushed ice (500 g). The temperature is allowed to rise to 20° C. and the product is drained and washed with water (6×500 cc).

The wet product is recrystallized in ethanol (1.2 liters). 7-Chloro-6-fluoro-3,4-dihydrocarbostyril (108 g) is obtained in the form of a beige solid, m.p. 215° C.

3'-Chloro-4'-fluoro-3-chloropropionanilide was prepared in the following manner:

A solution of 3-chloropropionyl chloride (127 g) in acetone (200 cc) is added with stirring in the course of 35 minutes to a solution, at a temperature in the region of 55°) C., of 3-chloro-4-fluoroaniline (291 g) in acetone (500 cc), and the mixture is maintained at this temperature for 2 hours. After cooling to approximately 20° C., the insoluble matter is removed by filtration and washed with acetone (2×200 cc). The combined filtrate and washings are poured with stirring into water (2 liters) and ice (1 kg). The temperature is allowed to rise to approximately 20° C. and the product is extracted with dichloromethane (4×500 cc). The combined organic extracts are washed with water (3×500 cc), dried over magnesium sulphate, stirred for 15 minutes with Norit vegetable charcoal (6 g), filtered through diatomaceous silica for filtration and concentrated under reduced pressure (2.7 kPa) at 50° C. The solid obtained is recrystallized in a mixture of cyclohexane (133 cc) and isopropyl ether (67 cc). 3'-Chloro-4'-fluoro-3-chloropropionanilide (176 g) is obtained in the form of a beige solid, m.p. 94° C., which is used without further treatment for the subsequent steps.

EXAMPLE 2

(RS)-1-Cyclopropyl-7-fluoro-4-oxo-8-(3-phenyl-1-piperazinyl)-1,4-dihydrobenzo[b][1,8]-naphthyridine-3-carboxylic acid was prepared under the conditions of Example 11 below, but starting with 8-chloro-1-cyclopropyl-7-fluoro-4-1,4-dihydrobenzo[b][1,8]naphthyridine-3-carboxylic acid (2 g), (RS)-2-phenylpiperazine (4.9 g) and triethylamine (1.7 cc). After recrystallization in a mixture of dimethylformamide (40 cc) and ethanol (50 cc), (RS)-1-cyclopropyl-7-fluoro-4-oxo-8-(3-phenyl-1-piperazinyl)-1,4-dihydrobenzo[b][1,8]naphthyridine-3-carboxylic acid (1.16 g) is obtained in the form of a yellow solid, m.p. 254° C.

8-Chloro-1-cyclopropyl-7-fluoro-4-oxo-1,4-dihydrobenzo[b][1,8]naphthyridine-3-carboxylic acid is prepared under the conditions of Example 1, but starting with 8-chloro-1-cyclopropyl-3-ethoxycarbonyl-7-fluoro-4-oxo-1,4-dihydrobenzo[b][1,8]naphthyridine (6.1 g). 8-Chloro-1-cyclopropyl-7-fluoro-4-oxo-1,4-dihydrobenzo[b][1,8]naphthyridine-3-carboxylic acid (4.85 g) is obtained in the form of a yellow solid, m.p. 330° C., which is used without further purification for the subsequent steps.

8-Chloro-1-cyclopropyl-3-ethoxycarbonyl-7-fluoro-4-oxo-1,4-dihydrobenzo[b][1,8]naphthyridine is prepared under the following conditions:

A solution of ethyl 2-(2,7-dichloro-6-fluoro-3-quinolinecarbonyl)-3-(dimethylamino)acrylate (20.6 g) and cyclopropylamine (6 g) in trichloromethane (100 cc) is stirred at a temperature in the region of 20° C. for 24 hours. The reaction mixture is concentrated under reduced pressure (2.7 kPa) at 50° C. The residue is taken up with ethanol (180 Zcc) and DBU (10 g) and the solution obtained heated to a temperature in the region of 78° C. for 4 hours. After cooling to a temperature in the region of 20° C., the precipitate obtained is drained and washed with ethanol (2×60 cc). 8-Chloro-1-cyclopropyl-3-ethoxycarbonyl-7-fluoro-4-oxo-1,4-di hydrobenzo[b][1,8]naphthyridine (13.65 g) is obtained in the form of a pale yellow solid, m.p. 256° C., which is used without further purification for the subsequent steps.

EXAMPLE 3

(RS)-7-Fluoro-1-(2-fluoroethyl)-4-oxo-8-(3-phenyl-1-piperazinyl)-4-oxo-1,4-dihydrobenz o[b][1,8]-naphthyridine-3-carboxylic acid was prepared under the following conditions:

A suspension of 7,8-difluoro-1-(2-fluoroethyl)-4-oxo-1,4-dihydrobenzo[b][1,8]-naphthyridine-3 -carboxylic acid (0.95 g) and (RS)-2-phenylpiperazine (1.05 g) in dimethyl sulphoxide (10 cc) is heated to a temperature in the region of 100° C. with stirring for 20 minutes. After cooling to approximately 20° C., the insoluble matter is drained and washed with ethanol (3×10 cc) at approximately 70° C. The expected product (1.3 g) is obtained in the form of a yellow solid, decomposing at 305° C.

7,8-Difluoro-1-(2-fluoroethyl)-4-oxo-1,4-dihydrobenzo[b][1,8]naphthyridine-3-carboxylic acid was prepared in the following manner:

A suspension of 3-ethoxycarbonyl-7,8-difluoro-1-(2-fluoroethyl)-4-oxo-1,4-dihydrobenzo[b][1,8]naphthyridine (2.3 g) in acetic acid (20 cc) and 5 N hydrochloric acid (20 cc) is heated with stirring to a temperature in the region of 100° C. for 1 hour. The insoluble matter is drained at approximately 70° C. and washed with water (3×10 cc) and ethanol (3×10 cc). The expected product (1.47 g) is obtained in the form of a beige solid, m.p. 291° C.

3-Ethoxycarbonyl-7,8-difluoro-1-(2-fluoroethyl)-4-oxo-1,4-dihydrobenzo[b][1,8]-naphthyridi ne was prepared in the following manner:

Ethyl 2-(2-chloro-6,7-difluoro-3-quinolinecarbonyl)-3-(dimethylamino)acrylate (2.58 g) is added at approximately 10° C. to a stirred mixture of 2-fluoroethylamine hydrochloride (1.46 g) and triethylamine (2.06 cc) in trichloromethane (30 cc). After 16 hours' stirring at approximately 20° C., the mixture is concentrated under reduced pressure (20 kPa) at a temperature in the region of 50° C. The residue is dissolved in ethanol (30 cc) and treated with triethylamine (2.3 cc). The mixture is heated with stirring to approximately 75° C. The insoluble matter is drained and washed with ethanol (3×5 cc); the expected product (2.3 g) is obtained in the form of a beige solid, m.p. 266° C., which was used without further purification for the subsequent steps.

Ethyl 2-(2-chloro-6,7-difluoro-3-quinolinecarbonyl)-3-(dimethylamino)acrylate may be obtained as described below in Example 39.

EXAMPLE 4

A suspension of 8-chloro-7-fluoro-1-methyl-4-oxo-1,4-dihydrobenzo[b][1,8]naphthyridine-3-carboxylic acid (1.6 g) and (RS)-2-(4-fluorophenyl)piperazine (3.7 g) in pyridine (16 cc) is heated to a temperature in the region of 115° C. for 24 hours. The reaction mixture is concentrated under reduced pressure (20 kPa) at approximately 60° C. The residue is taken up with ethanol (40 cc) and concentrated again under reduced pressure under the above conditions. The solid obtained is taken up with water (10 cc), treated with 10% strength acetic acid (1.75 cc), drained and washed with water (2×10 cc) and ethanol (2×10 cc). After 2 recrystallizations in dimethylformamide (10 cc each time), (RS)-7-fluoro-8-[3-(4-fluorophenyl)-1-piperazinyl]-1-methyl-4-oxo-1,4-dihydrobenzo[b ][1,8]naphthyridine-3-carboxylic acid (1.1 g) is obtained in the form of a yellow solid, m.p. 270°-275° C.

(RS)-2-(4-Fluorophenyl)piperazine was prepared according to the process described for (RS)-2-phenylpiperazine by R. Roderick et al., J. Med. Chem., 9, 181 (1966).

Starting with (RS)-2-(4-fluorophenyl)-3-oxo-piperazine (20 g) and lithium aluminium hydride (7.8 g) in ethyl ether (1.5 liters), (RS)-2-(4-fluorophenyl)-piperazine (11 g) is obtained in the form of a beige solid, m.p. 110°-112° C.

Starting with ethyl 1-bromo-1-(4-fluorophenyl)acetate (65 g) and ethylenediamine (30 g), (RS)-2-(4-fluorophenyl)-3-oxopiperazine (30 g) is obtained in the form of a colorless solid, m.p. 115° C.

Ethyl 1-bromo-1-(4-fluorophenyl)acetate was prepared according to J. W. Epstein et al., J. Med. Chem., 24, 481 (1981) starting with ethyl (4-fluorophenyl)acetate.

Ethyl (4-fluorophenyl)acetate was prepared according to the method described by J. W. Corse et al., J. Am. Chem. Soc., 70, 2837 (1948).

EXAMPLE 5

A solution of (RS)-7-fluoro-8-[3-(4-fluorophenyl)-1-piperazinyl]-1-methyl-4-oxo-1,4-dihy drobenzo[b][1,8-]naphthyridine-3-carboxylic acid (2.1 g) in 98% strength formic acid (1.8 cc) and 30% strength aqueous formaldehyde solution (4.4 cc) is heated to a temperature in the region of 100° C. for 2 hours. The reaction mixture is concentrated under reduced pressure (20 kPa) at approximately 50° C., treated with water (10 cc) and 2 N aqueous potassium hydroxide solution (1.2 cc) and heated to approximately 100° C. for 2 minutes. After cooling to a temperature in the region of 20° C., the insoluble matter is drained and washed with water (2×20 cc). After 2 recrystallizations in dimethylformamide (15 cc each time), (RS)-7-fluoro-b 8-[3-(4-fluorophenyl)-4-methyl-1-piperazinyl]-1-methyl-4-oxo-1,4-di hydrobenzo[b][1,8]naphthyridine-3-carboxylic acid (1.3 g) is obtained in the form of a yellow solid, decomposing at 313°-314° C.

EXAMPLE 6

The reaction is performed under the conditions of Example 16, but starting with 7,8-difluoro-1-methyl-4-oxo-1,4-dihydrobenzo[b][1,8]-naphthyridine-3-carboxylic acid (1.3 g) and (RS)-2-(3-fluorophenyl)piperazine (1.8 g). After 1 recrystallization in dimethylformamide (50 cc) containing ethanol (50%), (RS)-7-fluoro-8-[3-(3-fluorophenyl)-1-piperazinyl]-1-methyl-4-oxo -1,4-dihydrobenzo[b][1,8]naphthyridine-3-carboxylic acid (1.74 g) is obtained in the form of a yellow solid, m.p. 254° C.

EXAMPLE 7

The reaction is performed under the conditions of Example 4, but starting with 8-chloro-1-ethyl-7-fluoro-4-oxo-1,4-dihydrobenzo[b][1,8 ]-naphthyridine-3-carboxylic acid (1.5 g) and (RS)-2-(4-fluorophenyl)piperazine (3.4 g) in pyridine (15 cc). (RS)-1-Ethyl-7-fluoro-4-oxo-8-[3-(4-fluorophenyl)-1-piperazinyl]-1,4-dihydrobenzo[b][1,8]naphthyridine-3-carboxylic acid (0.92 g) is obtained in the form of a yellow solid, m.p. 298° C.

8-Chloro-1-ethyl-7-fluoro-4-oxo-1,4-dihydrobenzo[b][1,8]naphthyridine-3-carboxylic acid was prepared under the conditions of Example 1, but starting with 8-chloro-7-fluoro-3-ethoxycarbonyl-1-ethyl-4-oxo-1,4-dihydrobenzo[b][1,8]naphthyridine (10.5 g). 8-Chloro-1-ethyl-7-fluoro-4-oxo-1,4-dihydrobenzo[b][1,8]naphthyridine-3-carboxylic acid (9.3 g) is ьbtained in the form of a beige solid, m.p. 380° C., which is used without further purification for the subsequent steps.

8-Chloro-3-ethoxycarbonyl-1-ethyl-7-fluoro-4-oxo-1,4-dihydrobenzo[b][1,8]naphthyridine was prepared in the following manner:

Ethylamine (16 g) is added in the course of 5 minutes at between 10° and 15° C. to a stirred suspension of ethyl 2-(2,7-dichloro-6-fluoro-3-quinolinecarbonyl)-3-(dimethylamino)acrylate (13.5 g) in ethanol (135 cc), the temperature is allowed to rise to approximately 20° C., DBU (0.5 g) is added and the mixture is heated with stirring for 2 hours to a temperature in the region of 75° C. After cooling to a temperature in the region of 20° C., the precipitate is drained and washed with ethanol (2×100 cc) and ethyl ether (2×100 cc). 8-Chloro-3-ethoxycarbonyl-1-ethyl-7-fluoro-4-oxo-1,4-dihydrobenzo[b][1, 8]naphthyridine (10.4 g) is obtained in the form of a yellow solid, m.p. 300°-301° C., which is used without further purification for the subsequent steps.

EXAMPLE 8

Working under the conditions of Example 16, but starting with 1-ethyl-7,8-difluoro-4-oxo-1,4-dihydrobenzo[b][1,8]naphthyridine-3-carboxylic acid (1.5 g) and (RS)-2-(3-fluorophenyl)piperazine (1.98 g), (RS)-1-ethyl-7-fluoro-8-[3-(3-fluorophenyl)-1-piperazinyl]-4-oxo-1,4-dihydrobenzo[b][1,8]-naphthyridine-3-carboxylic acid (2 g) is obtained in the form of a yellow solid, m.p. 284° C.

1-Ethyl-7,8-difluoro-4-oxo-1,4-dihydrobenzo[b][1,8-]naphthyridine-3-carboxylic acid was prepared under the same conditions as in Example 17, but starting with 3-ethoxycarbonyl-1-ethyl-7,8-difluoro-4-oxo-1,4-dihydrobenzo[b][1,8]naphthyridine (8 g). The expected product (6.70 g) is obtained in the form of a yellow solid, decomposing at 330° C.

3-Ethoxycarbonyl-1-ethyl-7,8-difluoro-4-oxo-1,4-dihydrobenzo[b][1,8]naphthyridine may be obtained as described below in Example 32.

(RS)-2-(3-Fluorophenyl)piperazine was prepared according to the method described in French Patent Application 2,351,108. Starting with 3-fluorophenylglyoxal (24 g), the expected product (6.3 g) is obtained in the form of a yellow oil.

3-Fluorophenylglyoxal was prepared according to the method described by Nathan Kornblum et al., J. Am. Chem. Soc., 79, 6562 (1957). Starting with 3'-fluoro-2-bromoacetophenone (40 g), the expected product (24 g) is obtained in the form of a yellow oil.

3'-Fluoro-2-bromoacetophenone was prepared according to the method described by D.V.C. Awang et al., Canad. J. Chem. 47, 706, (1969). Starting with 3'-fluoroacetophenone (25.8 g), the expected product (40 g) is obtained in the form of a greenish oil.

EXAMPLE 9

Working under the conditions of Example 16, but starting with 1-ethyl-7,8-difluoro-4-oxo-1,4-dihydrobenzo[b][1,8]naphthyridine-3-carboxylic acid (1.5 g) and (RS)-2-(2-fluorophenyl)piperazine (1.5 g), (RS)-1-ethyl-7-fluoro-8-[3-(2-fluorophenyl)-1-piperazinyl-4-oxo-1,4-dihydrobenzo[b][1,8]-naphthyridine-3-carboxylic acid (2 g) is obtained in the form of a yellow solid, m.p. 306° C.

. (RS)-2-(2-Fluorophenyl)piperazine was prepared according to the same methods as used in Example 8. Starting with 2-fluorophenylglyoxal (26.8 g), (RS)-2-(2-fluorophenyl)piperazine (6 g), m.p. 70° C., is obtained.

Starting with 2'-fluoro-2-bromoacetophenone (40.3 g), 2-fluorophenylglyoxal (26.8 g) is obtained, and is used without further purification for the subsequent steps.

Starting with 2'-fluoroacetophenone (20 g), 2'-fluoro-2-bromoacetophenone (32.6 g) is obtained in the form of a greenish oil, which is used without further purification for the subsequent steps.

EXAMPLE 10

(RS)-1-Cyclopropyl-7-fluoro-8-[3-(4-fluorophenyl)-1-piperazinyl]-4-oxo-1,4-dihydrobenzo [b][1,8]naphthyridine-3-carboxylic acid was prepared under the conditions of Example 11 below, but starting with 8-chloro-1-cyclopropyl-7 fluoro-4-oxo-1,4-dihydrobenzo[b][1,8]naphthyridine-3-carboxylic acid (2 g), (RS)-2-(4-fluorophenyl)piperazine (6.534 g) and triethylamine (9 cc). The reaction mixture is concentrated under reduced pressure (20 kPa) at a temperature in the region of 60° C. The dry extract is taken up with water (20 cc) and acetic acid (0.5 cc). The insoluble matter is drained and washed with water (2×5 cc). After 1 recrystallization in a mixture of dimethylformamide (37 cc) and ethanol (37 cc), (RS)-1-cyclopropyl-7-fluoro-8-[3-(4-fluorophenyl) -1-piperazinyl]-4-oxo-1,4-dihydrobenzo[b][1,8]-naphthyridine-3-carboxylic acid (1.07 g) is obtained in the form of a yellow solid, m.p. 306° C.

EXAMPLE 11

A suspension of 8-chloro-7-fluoro-1-methyl-4-oxo-1,4-dihydrobenzo[b][1,8]naphthyridine-3-carboxylic acid (1.84 g) in pyridine (20 cc), (RS)-2-(4-methylphenyl)piperazine (5.83 g) and triethylamine (1.24 g) is heated to a temperature in the region of 115° C. for 37 hours. After cooling to approximately 20° C., the insoluble matter is drained and washed with ethanol (2×5 cc) and ethyl ether (2×5 cc). After recrystallization in dimethylformamide (25 cc), (RS)-7-fluoro-1-methyl-8-[3-(4-methylphenyl)-1-piperazinyl]-4-oxo-1,4-dihydrobenzo[b][1,8]naphthyridine-3-carboxylic acid (0.8 g) is obtained in the form of a yellow solid, decomposing at 282° C.

2-(4-Methylphenyl)piperazine was prepared according to the method described in Patent Application FR 2,351,108: starting with 4-methylphenylglyoxal (38.8 g) (prepared from 4-methylacetophenone), (RS)-2-(4-methylphenyl)piperazine (11.55 g) is obtained in the form of a yellow solid, m.p. 96°-97° C.

EXAMPLE 12

A suspension of (RS)-7,8-difluoro-1-methyl-4-oxo-1,4-dihydrobenzo[b][1,8]naphthyridine-3-carboxylic acid (1.45 g) and (RS)-2-(4-methoxyphenyl)piperazine (1.92 g) in dimethyl sulphoxide (14 cc) is heated with stirring to a temperature in the region of 90° C. for 2 hours. After cooling to approximately 20° C., water (20 cc) is added to the reaction mixture. The insoluble matter is drained and washed with water (2×5 cc). After 1 recrystallization in dimethylformamide (150 cc), (RS)-7-fluoro-8-[3-(4-methoxyphenyl)-1-piperazinyl]-1-methyl-4-oxo-1,4-dihydrobenzo[b][1,8]-naphthyridine-3-carboxylic acid (1.35 g) is obtained in the form of a yellow solid, decomposing at 312° C.

7,8-Difluoro-1-methyl-4-oxo-1,4-dihydrobenzo[b][1,8]naphthyridine-3-carboxylic acid is prepared in the following manner:

A suspension of 3-ethoxycarbonyl-7,8-difluoro-1-methyl-4-oxo-1,4-dihydrobenzo[b][1,8]-naphthyridine (8 g) in 17.5% strength aqueous hydrochloric acid solution (80 cc) and acetic acid (80 cc) is heated with stirring to a temperature in the region of 100° C. for 1 hour and a half. After cooling to approximately 20° C., the solid is drained and washed with water (6×100 cc). After 1 recrystallization in dimethylformamide (160 cc), 7,8-difluoro-1-methyl-4-oxo-1,4-dihydrobenzo[b][1,8-]naphthyridine-3 -carboxylic acid (6.44 g) is obtained in the form of a yellow solid, decomposing at 360° C.

3-Ethoxycarbonyl-7,8-difluoro-1-methyl-4-oxo-1,4-dihydrobenzo[b][1,8]naphthyridine may be obtained as described below in Example 19.

(RS)-2-(4-Methoxyphenyl)piperazine was prepared according to the method described in Patent Application FR 2,351,1-8, starting with 2-(4-methoxyphenyl)-glyoxal (23.4 g) and ethylenediamine (10.26 g); (RS)-2-(4-methoxyphenyl)piperazine (6.21 g) is obtained in the form of an oily product which is used without further treatment.

4-Methoxyphenylglyoxal may be prepared according to the method described by Nathan Kornblum et al., J. Am. Chem. Soc., 79, 6562 (1957). Starting with 2-bromo-4'-methoxyacetophenone (45.4 g) in dimethyl sulphoxide (200 cc), 4-methoxyphenylglyoxal (23.4 g) is obtained in the form of an orange-colored oil, which is used without further purification for the subsequent steps.

2-Bromo-4'-methoxyacetophenone was prepared according to NG.PH. Buu-Hoï et al., J. Chem. Soc., 255, (1951).

EXAMPLE 13

A suspension of 7,8-difluoro-1-methoxy-4-oxo-1,4-dihydrobenzo[b][1,8]naphthyridine-3-carboxylic acid (2 g) and (RS)-2-phenylpiperazine (2.1 g) in dimethyl sulphoxide (30 cc) is heated with stirring for 15 minutes to approximately 50° C. After cooling to approximately 20° C., the reaction mixture is poured into water (100 cc) and treated with acetic acid (1.2 cc). The insoluble matter is drained, washed with water (3×10 cc) and recrystallized in dimethylformamide (80 cc). (RS)-7-Fluoro-1-methoxy-4-oxo-8-(3-phenyl-1-piperazinyl)-1,4-dihydrobenzo[b][1,8]naphthyridine-3-carboxylic acid (2 g) is obtained in the form of a yellow solid, decomposing at 284° C.

7,8-Difluoro-1-methoxy-4-oxo-1,4-dihydrobenzo[b][1,8]naphthyridine-3-carboxylic acid is prepared under the following conditions.

A suspension of 3-ethoxycarbonyl-7,8-difluoro-1-methoxy-4-oxo-1,4-dihydrobenzo[b][1,8]-naphthyridine (2.78 g) in 17.5% strength hydrochloric acid (30 cc) and acetic acid (30 cc) is heated to a temperature in the region of 100° C. for 1 hour. After cooling to approximately 20° C., the reaction mixture is poured into water (100 cc). The precipitate formed is drained and washed with water (3×+cc) and ethanol (2×5cc). After 1 recrystallization in dimethylformamide (100 cc) containing ethanol (20%), 7,8-difluoro-1-methoxy-4-oxo-1,4-dihydrobenzo[b][1,8]-naphthyridine-3-carboxylic acid (2.03 g) is obtained in the form of a yellow solid, m.p. 325°-327° C.

3-Ethoxycarbonyl-7,8-difluoro-1-methoxy-4-oxo-1,4-dihydrobenzo[b][1,8]naphthyridine is prepared under the following conditions:

A suspension of methoxylamine hydrochloride (1.7 g) in trichloromethane (40 cc) is treated with triethylamine (2.13 g). After 15 minutes' stirring at a temperature in the region of 20° C., the solution obtained is treated with ethyl 2-(2-chloro-6,7-difluoro-3-quinolinecarbonyl)-3-(dimethylamino)acrylate (3.69 g) and stirred for 4 hours and a half at approximately 20° C. The reaction mixture is concentrated to dryness under reduced pressure (20 kPa) at a temperature in the region of 50° C. The residue is taken up with ethanol (70 cc) and triethylamine (3.6 g) and heated for 30 minutes to a temperature in the region of 75° C. After cooling to approximately 20° C., the precipitate obtained is drained and washed with ethanol (3×30 cc). 3-Ethoxycarbonyl-7,8-difluoro-1-methoxy-4-oxo-1,4-dihydrobenzo[b][1,8]naphthyridine (2.67 g) is obtained in the form of a pale yellow solid, m.p. 266°-268° C.).

Ethyl 2-(2-chloro-6,7-difluoro-2-quinolinecarbonyl)-3-(dimethylamino)acrylate may be obtained as described below in Example 20.

EXAMPLE 14

(RS)-8-[3-(4-Cyanophenyl)-1-piperazinyl]-7-fluoro-1-methyl-4-oxo-1,4-dihydrobenzo[b][1,8]-naphthyridine-3-carboxylic acid was prepared under the conditions of Example 11, but starting with 8-chloro-7-fluoro-1-methyl-4-oxo-1,4-dihydrobenzo[b][1,8]-naphthyridine-3-carboxylic acid (1.84 g), (RS)-2-(4-cyanophenyl)piperazine (5.61 g) and triethylamine (1.7 cc). (RS)-8-[3-(4-Cyanophenyl)-1-piperazinyl]-7-fluoro-1-methyl-4-oxo-1,4-dihydrobenzo[b][1,8]-naphthyridine-3-carboxylic acid (1.15 g) is obtained in the form of a yellow solid, decomposing at 332° C.

(RS)-2-(4-Cyanophenyl)piperazine may be prepared according to the method described in Patent Application FR 2,351,108, starting with 4-cyanophenylglyoxal (45 g); 2-(4-cyanophenyl)piperazine (9.4 g) is obtained in the form of an orange-colored oil, which is used without further treatment for the subsequent steps. 4-Cyanophenylglyoxal is prepared from 4-cyanoacetophenone.

EXAMPLE 15

Using the procedure described in Example 16, but starting with 7,8-difluoro-1-methyl-4-oxo-1,4-dihydrobenzo[b][1,8]naphthyridine-3-carboxylic acid (1.16 g) and (RS)-2-[4-(methoxymethyl)phenyl]piperazine (1.82 g), (RS)-7-fluoro-8-{3-[4-(methoxymethyl)-phenyl]-1-piperazinyl}-1-methyl-4-oxo -1,4-dihydrobenzo[b][1,8]-naphthyridine-3-carboxylic acid (1.70 g) is obtained in the form of a yellow solid, decomposing at 284° C.

(RS)-2-[4-Methoxymethyl)phenyl]piperazine was prepared according to the method described in Patent Application FR 2,351,108, but starting with 4-(methoxymethyl)phenylglyoxal (33.5 g) and ethylenediamine (13.48 g). The crude product was purified by chromatography on 230-400 mesh silica (750 g) suspended in a mixture of dichloromethane (70%), ethanol (26%) and triethylamine (4%) and elution with the same mixture (1.8 liters). After concentration of the eluate under reduced pressure (20 kPa) at approximately 50° C., the expected product (12.15 g) was obtained in the form of an orange-colored solid, m.p. 79° C.

4-(Methoxymethyl)phenylglyoxal was prepared according to the method described in Patent Application FR 2,351,108, but starting with 4-(methoxymethyl)-acetophenone (30.8 g) and selenium dioxide (24 g). The expected product (30 g) was obtained in the form of a brown oil, which was used without further purification for the subsequent steps.

4-(Methoxymethyl)acetophenone was prepared according to the method described by H. B. HASS et al., J. Am. Chem. Soc. 71, 1767 (1949), starting with 4-(methoxymethyl)cyanobenzene obtained from 4-cyanobenzyl bromide.

EXAMPLE 16

A suspension of 7,8-difluoro-1-methyl-4-oxo-1,4-dihydrobenzo[b][1,8]naphthyridine-3-carboxylic acid (1.015 g) and (RS)-2-[4-(2-hydroxyethoxy)phenyl]-piperazine (1.7 g) in dimethyl sulphoxide (15 cc) is heated with stirring to a temperature in the region of 100° C. for 2 hours and a half. After cooling to approximately 20° C., the suspension is treated with water (30 cc), drained and washed with water (3×10 cc). After one recrystallization in dimethylformamide (15 cc), (RS)-7-fluoro-8-{3-[4-(2-hydroxyethoxy)phenyl]-1-piperazinyl}-1-methyl-4-oxo-1,4-dihydrobenzo[b][1,8-]naphthyridine-3-carboxylic acid (1.2 g) is obtained in the form of a yellow solid, m.p. 276° C.

(RS)-2-[4-(2-Hydroxyethoxy)phenyl]piperazine may be prepared according to the method described in Patent Application FR 2,351,1-8, starting with 2-[4-(2-hydroxyethoxy)phenyl]glyoxal (18.5 g) and ethylenediamine (6.86 g). (RS)-2-[4-(2-Hydroxyethoxy)-phenyl]-piperazine (4 g) is obtained in the form of a beige solid, m.p. 141° C.

2-[4-(2-Hydroxyethoxy)phenylglyoxal may be prepared according to the method described by Nathan Kornblum et al., J. Am. Chem. Soc., 79, 6562 (1957). Starting with 4'-(2-hydroxyethoxy)-2-bromoacetophenone (30.5 g), 2-[4-(2-hydroxyethoxy)phenyl]glyoxal (18.5 g) is obtained in the form of a yellow oil, which is used without further purification for the subsequent steps.

4'-(2-Hydroxyethoxy)-2-bromoacetophenone may be prepared according to the method described by NG.PH. Buu-Hoï et al., J. Chem. Soc., 255 (1951). Starting with 4-(2-hydroxyethoxy)acetophenone (27 g), 4'-(2-hydroxyethoxy)-2-bromoacetophenone (28.85 g) is obtained in the form of a beige solid, m.p. 78° C.

4-(2-Hydroxyethoxy)acetophenone was prepared according to C. Rufer et al., J. Med. Chem., 18(3), 253, (1975).

EXAMPLE 17

Working under the conditions of Example 16, but starting with 7,8-difluoro-1-methyl-4-oxo-b 1,4-dihydrobenzo[b][1,8]naphthyridine-3-carboxylic acid (1.45 g) and (RS)-2-(3,4-dimethylphenyl)piperazine (2.09 g), (RS)-7-fluoro-1-methyl-8-[3-(3,4-dimethylphenyl)-1-piperazinyl]-4-oxo-1,4dihydrobenzo[b][1,8]naphthyridine-3-carboxylic acid (2.15 g) is obtained in the form of a yellow solid, m.p. 276° C.

(RS)-2-(3,4-Dimethylphenyl)piperazine was prepared according to the method described in Patent Application FR 2,351,108. Starting with 3,4-dimethylphenylglyoxal (42.4 g), (RS)-2-(3,4-dimethylphenyl)piperazine (7.9 g) is obtained in the form of a beige solid, m.p. 98°-100° C.

3,4-dimethylphenylglyoxal may be prepared according to the method described by Nathan Kornblum et al., J. Am. Chem. Soc., 79, 6562 (1957). Starting with 3',4'-dimethyl-2-bromoacetophenone (60 g), 3,4-dimethylphenylglyoxal (40.4 g) is obtained in the form of an oil.

3',4'-Dimethyl-2-bromoacetophenone was prepared according to the method described by R. M. Laird and R. E. Parker, J. Am. Chem. Soc. 83, 4277, (1961).

EXAMPLE 18

Working under the conditions of Example 16, but starting with 7,8-difluoro-1-methyl-4-oxo-1,4-dihydrobenzo[b][1,8]naphthyridine-3-carboxylic acid (1.16 g) and (RS)-2-(4-amino-3-methoxyphenyl)piperazine (1.82 g), (RS)-8-[3-(4-amino-3-methoxyphenyl)-1-piperazinyl]-1-methyl-4-oxo-1,4-dihydrobenzo[b][1,8]-naphthyridine-3-carboxylic acid (1.40 g) is obtained in the form of a yellow solid, decomposing at 259° C.

(RS)-2-(4-Amino-3-methoxyphenyl)piperazine was prepared in the following manner:

A solution of sodium hydrosulphite (53 g) in water (200 cc) is added in the course of 10 minutes to a solution, heated with stirring to approximately 75° C., of (RS)-2-(3-methoxy-4-nitrophenyl)piperazine (18 g) in ethanol (150 cc). The mixture is kept stirring at the same temperature for 1 hour. The reaction mixture is concentrated under reduced pressure (20 kPa) at approximately 60° C. The residue is taken up with 3.75 N aqueous sodium hydroxide solution (150 cc) and potassium carbonate (50 g). The mixture is extracted with trichloromethane (4×100 cc). The combined organic extracts are dried over magnesium sulphate, filtered and concentrated under reduced pressure (20 kPa) at approximately 40° C. The expected product (13 g) is obtained in the form of a brown oil, which is used without further purification for the subsequent steps.

(RS)-2-(3-Methoxy-4-nitrophenyl)piperazine was prepared according to the method described in Patent Application FR 2,351,108, but starting with 3-methoxy-4-nitrophenylglyoxal (36 g) and ethylenediamine (12.1 g). The crude product is purified by chromatography on 230-400 mesh silica (800 g) suspended in a mixture of dichloromethane (70%), ethanol (26%) and triethylamine (4%) and elution with the same mixture (2 liters). After concentration of the eluate under reduced pressure (20 kPa) at approximately 50° C., the expected product (18 g) is obtained in the form of a red oil, which was used without further purification for the subsequent steps.

3-Methoxy-4-nitrophenylglyoxal was prepared according to the method described in Patent Application FR 2,351,108, but starting with 3-methoxy-4-nitroacetophenone (33.6 g) and selenium dioxide (22 g). The expected product (35 g) is obtained in the form of a brown oil, which was used without further purification for the subsequent steps.

3-Methoxy-4-nitroacetophenone was prepared according to the method described in S. African Patent 67/06,465.

EXAMPLE 19

A solution of (RS)-3-ethoxycarbonyl-7-fluoro-1-methyl-4-oxo-8-(3-phenyl-1-piperazinyl)-1,4-dihydrobenzo[b][1,8]naphthyridine (1.07 g) in acetic acid (10 cc) and 17.5% strength aqueous hydrochloric acid solution (10 cc) is heated to a temperature in the region of 100° C. for 40 minutes. The reaction mixture is concentrated to dryness under reduced pressure (20 kPa) at approximately 60° C. The dry extract is taken up with ethanol (10 cc), drained and washed with ethanol (2×10 cc) and ethyl ether (2×10 cc). The solid obtained is suspended in water (30 cc) and heated to a temperature in the region of 95° C. After the addition of 2 N aqueous potassium hydroxide (1.35 cc) and stirring for 30 minutes, the solid is drained at approximately 95° C. and washed with water (3×20 cc) at approximately 80° C., ethanol (3×15 cc) at approximately 60° C. and ethyl ether (3×20 cc). After 1 recrystallization in a mixture of dimethylformamide (12 cc) and ethanol (6 cc), (RS)-7-fluoro-1-methyl-4-oxo-8-(3-phenyl-1-piperazinyl)-1,4-dihydrobenzo[b][1,8]naphthyridine-3-carboxylic acid (0.7 g) is obtained in the form of a yellow solid, m.p. 265° C.

(RS)-3-Ethoxycarbonyl-7-fluoro-1-methyl-4-oxo-8-(3-phenyl-1-piperazinyl)-1,4-dihydrobenzo[b][1,8]naphthyridine may be prepared in the following manner:

A suspension of 3-ethoxycarbonyl-7,8-difluoro-1-methyl-4-oxo-1,4-dihydrobenzo[b][1,8]naphthyridine (0.8 g), sodium carbonate (0.265 g) and (RS)-2-phenylpiperazine (0.5 g) in dimethyl sulphoxide (25 cc) is heated to a temperature in the region of 95° C. for 2 hours. After cooling to approximately 20° C., the reaction mixture is poured into water (75 cc) and extracted with dichloromethane (4×50 cc). The combined organic extracts are washed with water (3×40 cc), dried over magnesium sulphate, filtered and concentrated to dryness under reduced pressure (20 kPa) at approximately 50° C. (RS)-3-Ethoxycarbonyl-7-fluoro-4-oxo-8-(3-phenyl-1-piperazinyl)-1,4-dihydrobenzo[b][1,8-]naphthyridine (1.07 g) is obtained in the form of a yellow solid, m.p. 220°-222° C., which is used without further purification for the subsequent steps.

3-Ethoxycarbonyl-7,8-difluoro-1-methyl-4-oxo-1,4-dihydrobenzo[b][1,8]naphthyridine is prepared in the following manner:

A solution of methylamine (11.3 g) at approximately 0° C. in ethanol (50 cc) is added in the course of 10 minutes at between 0° and 5° C. to a stirred suspension, maintained at a temperature in the region of 0° C., of ethyl 2-(2-chloro-6,7-difluoro-3-quinolinecarbonyl)-3-(dimethylamino)acrylate (22.3 g) in ethanol (480 cc), the mixture is stirred for 1 hour at between 0° and 5° C., the temperature is allowed to rise to approximately 25° C. and the mixture is stirred for a further 16 hours at the same temperature. The insoluble matter is drained and washed with ethanol (3×100 cc) and ethyl ether (2×100 cc). After 1 recrystallization in dimethylformamide (250 cc), 3-ethoxycarbonyl-7,8-difluoro-1-methyl-4-oxo-1,4-dihydrobenzo[b][1,8]naphthyridine (16 g) is obtained in the form of a yellow solid, m.p. 323°-324° C.

Ethyl 2-(2-chloro-6,7-difluoro-3-quinolinecarbonyl)-3-(dimethylamino)acrylate is prepared in the following manner:

A suspension of ethyl 3-(2-chloro-6,7-difluoro-3-quinolyl)-3-oxopropionate (6.17 g) in N,N-dimethylformamide dimethyl acetal (7.15 g) and ethyl acetate (60 cc) is heated to a temperature in the region of 75° C. for 1 hour 15 minutes. The reaction mixture is concentrated to dryness under reduced pressure (20 kPa) at approximately 50° C. The residue is taken up with isopropyl ether (50 cc), drained and washed with the same solvent (3×25 cc). Ethyl 2-(2-chloro-6,7-difluoro-3-quinolinecarbonyl)-3-(dimethyl amino)acrylate (6.65 g) is obtained in the form of an orange-colored solid, m.p. 140° C.

Ethyl 3-(2-chloro-6,7-difluoro-3-quinolyl)-3-oxopropionate is prepared in the following manner:

A suspension of 2-chloro-6,7-difluoroquinoline-3-carboxylic acid (14.13 g) in thionyl chloride (29 cc) and trichloromethane (220 cc) is heated to a temperature in the region of 60° C. for 4 hours. The solution obtained is concentrated to dryness under reduced pressure (20 kPa) at approximately 60° C. The residue obtained is taken up with n-hexene (75 cc), drained and washed with the same solvent (2×60 cc). The yellow solid obtained (14.4 g) is dissolved in tetrahydrofuran (115 cc). This solution is introduced dropwise, with stirring, in the course of 35 minutes at between 5° and 10° C. into a solution (70 cc) of magnesium chelate of ethyl monomalonate in tetrahydrofuran, prepared under the conditions described below. The temperature is allowed to rise to approximately 20 C. and the mixture is stirred for a further 2 hours under these conditions. The solution obtained is introduced dropwise, with stirring, in the course of 30 minutes and at a temperature in the region of 5° C. into 0.5 N sulphuric acid (560 cc). The temperature of the suspension obtained is allowed to rise to 20° C. and the mixture is stirred for a further 1 hour and a half at this temperature. The product is extracted with ethyl acetate (3×250 cc). The combined organic extracts are washed with water (2×250 cc), dried over magnesium sulphate, filtered and concentrated to dryness under reduced pressure (20 kPa) at 50° C. The residue obtained is taken up with n-hexane (50 cc) containing isopropyl ether (20%), drained, washed with the same mixture (10 cc) and recrystallized in isopropanol (60 cc) containing n-hexane (30%). Ethyl 3-(2-chloro-6,7-difluoro-3-quinolyl)-3-oxo-propionate (11.84 g) is obtained in the form of a cream-colored solid, m.p. 107° C.

Preparation of the magnesium chelate of ethyl monomalonate:

Absolute ethanol (2 cc), tetrachloromethane (0.1 cc) and ethyl monomalonate (1 g) are added gradually to magnesium turnings (2.78 g). After heating, a solution of ethyl monomalonate (9 g) in ethanol (180 cc) is added in the course of 15 minutes. The mixture is heated for 20 hours to a temperature in the region of 75° C. and concentrated under reduced pressure (20 kPa) at 50° C. The residue is taken up with toluene (2×100 cc) and concentrated under reduced pressure under the same conditions as above. The grey powder obtained is dissolved by adding anhydrous tetrahydrofuran so as to obtain a total volume of 70 cc.

2-Chloro-6,7-difluoro-3-quinolinecarboxylic acid was prepared in the following manner:

A solution of potassium permanganate (115 g) in water (1.215 liters) is added in the course of 1 hour to a stirred suspension, cooled to 10° C., of 2-chloro-6,7-difluoro-3-formyl-1,4-dihydro quinoline (70.18 g) in N aqueous potassium hydroxide solution (970 cc) while the temperature is maintained at between 10° and 14° C. The temperature is allowed to rise to approximately 20° C. and the mixture is stirred for a further 30 minutes at this temperature. Sodium dithionite (38.5 g) is added and the mixture is stirred for 10 minutes at a temperature in the region of 20° C., filtered through diatomaceous silica and washed with water (3×200 cc). The filtrate and the aqueous washing phases are combined and treated with 35% strength aqueous hydrochloric acid solution (140 cc). The precipitate formed is extracted with ethyl acetate (4×800 cc). The combined organic extracts are washed with water (2×500 cc), dried over magnesium sulphate, filtered and concentrated under reduced pressure (20 kPa) at 50° C. The residue is taken up with ethyl ether (400 cc), drained and washed with the same solvent (2×200 cc). 2-Chloro-6,7-difluoro-3-quinolinecarboxylic acid (49.2 g) is obtained in the form of a beige solid, m.p. 232° C., which is used without further purification for the subsequent steps.

2-Chloro-6,7-difluoro-3-formyl-1,4-dihydroquinoline was prepared in the following manner:

Phosphoryl chloride (76.9 cc) is added in the course of 30 minutes, with stirring and at between 10° and 15° C. to a mixture of trichloromethane (800 cc) and dimethylformamide (74.35 cc), and the mixture is stirred for 1 hour at a temperature in the region of 20° C. To the solution obtained, 6,7-difluoro-3,4-dihydrocarbostyril (65.8 g) is added in the course of 10 minutes at approximately 20° C. with vigorous stirring. The suspension obtained is heated to a temperature in the region of 60° C. and maintained at this temperature for 2 hours. The reaction mixture is concentrated under reduced pressure (20 kPa) at 50° C. until a pasty mixture is obtained. A mixture of ice (500 g) and water (500 cc) is added with vigorous stirring. The solid obtained is drained at approximately 5° C. and washed with water (3×300 cc) at 5° C. The wet product obtained and sodium acetate (60 g) are added simultaneously in the course of 1 hour to water (1.5 liters) at 90° C., so as to maintain the pH at approximately 6. The mixture is stirred for a further 30 minutes at 90° C., the temperature is allowed to fall to approximately 50° C. and the product is drained at this temperature and washed with water (3×300 cc) at approximately 20° C. 2-Chloro-6,7-difluoro-3-formyl-1,4-dihydroquinoline 70.18 g) is obtained in the form of a yellow solid, m.p. 260° C., which is used without further treatment for the subsequent steps.

6,7-Difluoro-3,4-dihydrocarbostyril is obtained in the following manner:

Aluminium chloride (134 g) is added with vigorous stirring to 3',4'-difluoro-3-chloropropionanilide (67 g) and then, after approximately 2 minutes, 3',4'-difluoro-3-chloropropionanilide (135.9 g) and aluminium chloride (272 g) are added again in small portions in the course of 15 minutes. The temperature rises spontaneously to approximately 60° C. and the reaction mixture becomes liquid. The mixture is then heated to 110° C. in the course of 20 minutes and maintained at between 110° C. and 120° C. for 2 hours. The reaction mixture (at approximately 110° C.) is poured in the course of 10 minutes with vigorous stirring into a mixture of 35% strength hydrochloric acid (840 cc) and crushed ice (1 kg). The temperature is allowed to rise to approximately 20° C. and the product is drained, washed with water (2×600 cc), ethanol (300 cc) at 5° C. and ethyl ether (2×400 cc) at approximately 20° C. 6,7-Difluoro-1,4-dihydrocarbostyril (131.58 g) is obtained in the form of a beige solid, m.p. 216° C., which is used without further treatment for the subsequent steps.

3',4'-Difluoro-3-chloropropionanilide is prepared in the following manner:

3-Chloropropionyl chloride (139.16 g) is added with stirring in the course of 1 hour and a half to a solution, heated to a temperature in the region of 55° C., of 3,4-difluoroaniline (125 g) in pyridine (80 cc) and acetone (1.5 liters), and the mixture is maintained at this temperature for 1 hour and a half. After cooling to approximately 20° C., the solution is poured with stirring into a mixture of water (1 liter) and crushed ice (500 g). The temperature is allowed to rise to approximately 20° C. and the product is extracted with dichloromethane (3×500 cc). The combined organic extracts are washed with N hydrochloric acid (500 cc) and water (5×500 cc), dried over magnesium sulphate, filtered and concentrated under reduced pressure (20 kPa) at approximately 50° C. The solid obtained is taken up in n-hexane (500 cc), drained and washed with the same solvent (2×100 cc). 3',4'-Difluoro-3-chloropropionanilide (202.9 g) is obtained in the form of a beige solid, m.p. 76° C., which is used without further purification for the subsequent steps.

(RS)-2-Phenylpiperazine was prepared according to the process described by W. R. Roderick et al., J. Med. Chem., 9, 181 (1966).

EXAMPLE 20

Working under the conditions of Example 25, but starting with (S)-3-ethoxycarbonyl-7-fluoro-1-methyl-4-oxo-8-(3-phenyl-1-piperazinyl)-1,4-dihydrobenzo[b][1,8]naphthyridine (0.6 g), and after recrystallization in dimethylformamide (13 cc) containing ethanol (30%), (S)-7-fluoro-1-methyl-4-oxo-8-(3-phenyl-1-piperazinyl)-1,4-dihydrobenzo[b][1,8]naphthyridine-3-carboxylic acid (0.44 g) is obtained in the form of a yellow solid, decomposing at 276°–278° C.

$[\alpha]_D^{20} = 39.3 + 0.8$ (c=1; acetic acid)

Working under the conditions of Example 25, but starting with 3-ethoxycarbonyl-7,8-difluoro-1-methyl-4-oxo-1,4-dihydrobenzo[b][1,8]naphthyridine (0.8 g) and (S)-2-phenylpiperazine (0.5 g), (S)-3-ethoxycarbonyl-7-fluoro-1-methyl-4-oxo-8-(3-phenyl-1-piperazinyl)-1,4-dihydrobenzo[b][1,8]naphthyridine (0.85 g) is obtained in the form of a yellow solid, mp. 226° C.

$[\alpha]_D^{20} = -45° \pm 1$ (c=0.5; acetic acid).

The synthesis of (S)-2-phenylpiperazine was performed according to the same process as that described in Example 22.

Starting with (S)-2-phenyl-1,4-bis(p-toluenesulphonyl)piperazine (14.9 g), (S)-2-phenylpiperazine (3.31 g) is obtained in the form of a colourless solid, m.p. 117° C.

$[\alpha]_D^{20} = +39° \pm 0.6$ (c=2; ethanol).

Starting with (S)-2-phenyl-1,4-bis(p-toluenesulphonyl)ethylenediamine (16.3 g), (S)-2-phenyl-1,4-bis(p-toluenesulphonyl)piperazine is obtained in the form of a colorless solid, m.p. 258° C.

$[\alpha]_D^{20} = -9.9° \pm 0.9$ (c=0.5; dimethylformamide).

Starting with (S)-2-phenylethylenediamine (17.5 g), (S)-2-phenyl-1,4-bis(p-toluenesulphonyl)ethylenediamine (22.5 g) is obtained in the form of a yellow solid, m.p. 164° C.

$[\alpha]_D^{20} = +17.2 \pm 0.7$ (c=0.7; dimethylformamide).

Starting with (S)-α-aminophenylacetamide (20 g), (S)-2-phenylethylenediamine (17.5 g) is obtained in the form of a yellow oil, which is used immediately for the subsequent step.

Starting with methyl (S)-2-phenylglycinate (45.1 g), (S)-α-aminophenylacetamide (21.5 g) is obtained in the form of a colorless solid, m.p. 137°–138° C.

$[\alpha]_D^{20} = +114° \pm 2$ (c=1; ethanol).

Starting with (S)-2-phenylglycine (45.3 g), methyl (S)-2-phenylglycinate (45.1 g) is obtained in the form of a yellow oil.

EXAMPLE 21

Working under the conditions of Example 20, but starting with (R)-3-ethoxycarbonyl-7-fluoro-1-methyl-4-oxo-8-(3-phenyl-1-piperazinyl)-1,4-dihydrobenzo[b][1,8]naphthyridine (66.3 g), and without recrystallization, (R)-7-fluoro-1-methyl-4-oxo-8-(3-phenyl-1-piperazinyl)-1,4-dihydrobenzo[b][1,8]naphthyridine-3-carboxylic acid (59.15 g) is obtained in the form of a yellow solid, decomposing at 276°-278° C.

$[\alpha]_D^{20} = +39.8 \pm 0.6$ (c=1; acetic acid).

Working under the conditions of Example 20, but starting with 3-ethoxycarbonyl-7,8-difluoro-1-methyl-4-oxo-1,4-dihydrobenzo[b][1,8]naphthyridine (51.6 g) and (R)-2-phenylpiperazine (31.7 g), (R)-3-ethoxycarbonyl-7-fluoro-1-methyl-4-oxo-8-(3-phenyl-1-piperazinyl)-1,4-dihydrobenzo[b][1,8]naphthyridine (66.86 g) is obtained in the form of a yellow solid, m.p. 221° C.

$[\alpha]_D^{20} = +43° \pm 1$ (c=0.5; acetic acid).

(R)-2-Phenylpiperazine may be prepared in the following manner:

A mixture of (R)-2-phenyl-1,4-bis(p-toluenesulphonyl)piperazine (10 g) and phenol (9.4 g) in 48% strength hydrobromic acid (100 cc) is heated with very vigorous stirring to a temperature in the region of 120° C. for 5 hours. After cooling to approximately 80° C., the reaction mixture is treated with water (250 cc), cooled to about 20° C. and washed with dichloromethane (5×100 cc). The aqueous phase is concentrated under reduced pressure (20 kPa) at approximately 80° C. The residue is taken up with ethyl acetate (100 cc), cooled to 5° C. and treated at between 5° and 20° C. with 30% strength aqueous sodium hydroxide (100 cc). The organic phase is separated and the aqueous phase extracted again with ethyl acetate (3×100 cc). The combined organic extracts are washed with 5N aqueous sodium hydroxide (4×20 cc), dried over magnesium sulphate, filtered and concentrated to dryness under reduced pressure (20 kPa) at approximately 30° C. The residue obtained is taken up with isopropyl ether (15 cc) at approximately 0° C., drained and washed at the same temperature with the same solvent (10 cc). (R)-2-Phenylpiperazine (2.3 g) is obtained in the form of a colorless solid, m.p. 117° C.

$[\alpha]_D^{20} = 38° \pm 0.6$ (c=2; ethanol).

(R)-2-Phenyl-1,4-bis(p-toluenesulphonyl)piperazine was prepared in the following manner:

A mixture of (R)-2-phenyl-1,4-bis(p-toluenesulphonyl)ethylenediamine (11 g) and potassium carbonate (13.82 g) in dimethylformamide (110 cc) is heated with stirring to 60° C. for 30 minutes, then treated with 1,2-dibromoethane (18.8 g) and heated to 115° C. for 1 hour. After cooling to approximately 20° C., the reaction mixture is poured into water (250 cc) and extracted with dichloromethane (3×200 cc). The combined organic extracts are washed with water (3×120 cc), dried over magnesium sulphate and concentrated under reduced pressure (20 kPa) at approximately 30° C. The residue is taken up with ethyl ether (50 cc), drained and washed with the same solvent (3×15 cc). The expected product (10.55 g) is obtained in the form of a colorless solid, m.p. 258° C.

$[\alpha]_D^{20} = +9.6° \pm 0.8$ (c=0.5; dimethylformamide).

(R)-2-Phenyl-1,4-bis(p-toluenesulphonyl)ethylenediamine was prepared according to the method described by Douglas G. Neilson et al., J. Chem. Soc. 393 (1966), but starting with (R)-2-phenylenediamine (7.5 g). The expected product (12.9 g) is obtained in the form of a yellow solid, m.p. 164° C.

$[\alpha]_D^{20} = 18.2 \pm 0.7$ (c=0.7; dimethylformamide).

(R)-2-Phenylethylenediamine was prepared according to the method described by H. C. Brown et al., J. Am. Chem. Soc. 86, 3566 (1964), but starting with (R)-α-aminophenylacetamide (11 g) and a 1M solution (293 cc) of borane in tetrahydrofuran. The expected product (7.5 g) is obtained in the form of an unstable yellow oil, which is used immediately for the subsequent step.

(R)-α-Aminophenylacetamide was prepared according to the method described by Douglas G. Neilson et al., J. Chem. Soc. 393 (1966). Starting with methyl (R)-2-phenylglycinate (27.9 g), and after 1 recrystallization in ethyl acetate (135 cc) containing methanol (26%), the expected product (12.93 g) is obtained in the form of a colorless solid, m.p. 137°-138° C.

$[\alpha]_D^{20} = -115° \pm 3$ (c=0.5; ethanol).

Methyl (R)-2-phenylglycinate was prepared according to the method described by Douglas G. Neilson et al., J. Chem. Soc. 393 (1966), but starting with (R)-2-phenylglycine (43 g) and thionyl chloride (22.8 cc) in methanol (85 cc), in the form of a yellow oil.

(R)-7-Fluoro-1-methyl-4-oxo-8-(3-phenyl-1-piperazinyl)-1,4-dihydrobenzo[b][1,8]naphthyridine-3-carboxylic acid monomethanesulphonate was prepared in the following manner:

A suspension of (R)-7-fluoro-1-methyl-4-oxo-8-(3-phenyl-1-piperazinyl)-1,4-dihydrobenzo[b][1,8]naphthyridine-3-carboxylic acid (3.5 g) in water (70 cc) is treated with a 0.1N aqueous solution (100 cc) of methanesulphonic acid and heated to approximately 90° C. After cooling to approximately 20° C., the insoluble matter is drained and washed with water (3×25 cc). The expected salt (3.9 g) is obtained in the form of a yellow solid, decomposing at 335°-340° C.

$[\alpha]_D^{20} = -19° \pm 2$ (c=0.2; water containing 50% of ethanol).

Choline (R)-7-fluoro-1-methyl-4-oxo-8-(3-phenyl-1-piperazinyl)-1,4-dihydrobenzo[b][1,8]naphthyridine-3-carboxylate was prepared in the following manner:

A 45% strength solution (2.72 cc) of choline in methanol is added to (R)-7-fluoro-1-methyl-4-oxo-8-(3-phenyl-1-piperazinyl)-1,4-dihydrobenzo[b][1,8]naphthyridine-3-carboxylic acid (3.5 g) suspended in methanol (30 cc). Isopropyl ether (200 cc) is added to the solution obtained. The precipitate is drained and washed with the same solvent (3×60 cc) and then with acetone (3×60 cc). The expected salt (3.97 g) is obtained in the form of a yellow solid, m.p. 234° C.

$[\alpha]_D^{20} = -33.9° \pm 0.9$ (c=1; methanol).

(R)-7-Fluoro-1-methyl-4-oxo-8-(3-phenyl-1-piperazinyl)-1,4-dihydrobenzo[b][1,8]naphthyridine-3-carboxylic acid monoisethionate was prepared in the following manner: a 1N aqueous solution (2.6 cc) of isethionic acid is added to a suspension of (R)-7-fluoro-1-methyl-4-oxo-8-(3-phenyl-1-piperazinyl)-1,4-dihydrobenzo[b][1,8]naphthyridine-3-carboxylic acid (1 g) in water (40 cc) containing ethanol (50%). After dissolution at approximately 80° C. and then cooling to approximately 10° C., the insoluble matter is drained and washed with water (2×15 cc) containing ethanol (50%), water (2×15 cc) and ethanol (3×15 cc). The expected salt (1 g) is obtained in the form of a yellow solid, decomposing at 334° C.

$[\alpha]_D^{20} = +111° \pm 6$ (c=0.1; dimethyl sulphoxide).

EXAMPLE 22

(−)-7-Fluoro-1-methyl-4-oxo-8-(3-phenyl-1-piperazinyl)-1,4-dihydrobenzo[b][1,8]naphthyridine-3-carboxylic acid (S) isomer was prepared in the same manner as (RS)-7-fluoro-1-methyl-4-oxo-8-(3-phenyl-1-piperazinyl)-1,4-dihydrobenzo[b][1,8]naphthyridine-3-carboxylic acid (Example 19), but starting with 3-ethoxycarbonyl-7,8-difluoro-1-methyl-4-oxo-1,4-dihydrobenzo[b][1,8]naphthyridine (4.4 g), (+)-2-phenylpiperazine (2.7 g) ($[\alpha]_D^{20} = +35.4° \pm 0.5$ (c=2; ethanol)) and sodium carbonate (1.48 g). A yellow solid (6.3 g), m.p. 226° C., is obtained.

After acid hydrolysis under the same conditions as those described for (RS)-3-ethoxycarbonyl-7-fluoro-1-methyl-4-oxo-8-(3-phenyl-1-piperazinyl)-1,4-dihydrobenzo[b][1,8]naphthyridine, (−)-7-fluoro-1-methyl-4-oxo-8-(3-phenyl-1-piperazinyl)-1,4-dihydrobenzo[b][1,8]naphthyridine-3-carboxylic acid (S) isomer (3.95 g) is obtained in the form of a yellow solid, m.p. 276°-278° C.

$[\alpha]_D^{20} = -40.4° \pm 1$ (c=1; acetic acid).

(−)-2-Phenylpiperazine (R) isomer and (+)-2-phenylpiperazine (S) isomer were prepared by the acid hydrolysis of 2 diastereoisomeric compounds (R and S) corresponding to the structure of a 1-(2-trifluoromethyl-2-methoxyphenylacetyl)-3-phenylpiperazine, arbitrarily designated A and B. The latter 2 compounds are obtained by the acylation of (RS)-2-phenylpiperazine with a chiral acid chloride ((−)-(R)-2-trifluoromethyl-2-methoxyphenylacetyl chloride). The preparation is as follows:

A solution of (−)-(R)-2-trifluoromethyl-2-methoxyphenylacetyl chloride (19.89 g) in trichloromethane (80 cc) is added dropwise, in the course of 25 minutes and with stirring to a solution, cooled to approximately −25° C., of (RS)-2-phenylpiperazine (12.77 g) in trichloromethane (220 cc) while the temperature is maintained at between −+° and −25° C. After 15 minutes stirring under these conditions, the temperature is allowed to rise to approximately 0° C., 2N aqueous sodium hydroxide (50 cc) is added at between 0° and 5° C., the temperature is allowed to rise to approximately 20° C. and water (150 cc) is added. The organic phase is separated and the aqueous phase extracted again with trichloromethane (2×200 cc). The combined organic extracts are washed with 0.5N sodium hydroxide (1×200 cc) and water (4×200 cc), dried over magnesium sulphate, filtered and concentrated to dryness under reduced pressure (20 kPa) at approximately 40° C. The residue (29.8 g) containing the two diastereoisomers A and B is dissolved in dichloromethane (500 cc). This mixture is separated by high performance liquid chromatography on 2 columns 57 mm in diameter and 300 mm long, each containing 55–105 μ silica (300 g), in 5 100-cc injections. Elution is performed with a mixture of dichloromethane containing ethanol (2%). The diastereoisomer A is eluted with this mixture (1 liter) in the fraction comprised between 2.5 and 3.5 liters. The diastereoisomer B is eluted with the same mixture (2 liters) in the fraction comprised between 4 and 6 liters. After concentration of each of the two fractions under reduced pressure (20 kPa) at approximately 50° C., there are obtained, respectively, compound A (13.62 g) in the form of a colorless solid, m.p. 102° C., and compound B (14 g), of the same appearance, m.p. 130° C. Compound A (13.62 g) is taken up with a mixture of 48% strength aqueous hydrobromic acid solution (140 cc) and acetic acid (26 cc) and heated for 30 hours to a temperature in the region of 110° C. The reaction mixture is concentrated to dryness under reduced pressure (20 kPa) at approximately 80° C. The residue obtained is taken up with ethyl acetate (200 cc). The suspension obtained is cooled to approximately 10° C. and treated at between 10° and 20° C. with 30% strength aqueous sodium hydroxide (160 cc). The organic phase is separated and the aqueous phase extracted again with ethyl acetate (3×100 cc). The combined organic extracts are washed with 4N aqueous sodium hydroxide (1×80 cc) and 30% strength aqueous sodium chloride solution (3×80 cc) and concentrated to dryness under reduced pressure. After the residue obtained has been taken up with a 10% strength aqueous solution (80 cc) of methanesulphonic acid and the organic phase extracted with ethyl acetate (3×100 cc), the aqueous phase is treated with 30% strength aqueous sodium hydroxide (120 cc) and extracted with ethyl acetate (4×150 cc). The combined organic extracts are washed with 30% strength aqueous sodium chloride solution (3×80 cc), dried over magnesium sulphate, filtered and concentrated under reduced pressure (20 kPa) at a temperature in the region of 50° C. The residue obtained is taken up with isopropyl ether (30 cc), drained and washed with the same solvent (10 cc). (+)-2-Phenylpiperazine (2.45 g) is obtained in the form of a colorless solid, m.p. 114° C.

$[\alpha]_D^{20} = +35.4° \pm 0.5$ (c=2; ethanol).

Compound B (14 g), treated under the same conditions as those described for the compound A, yields (−)-2-phenylpiperazine (3.08 g) in the form of a colourless solid, m.p. 114° C.

$[\alpha]_D^{20} = -37° \pm 0.5$ (c=2; ethanol).

EXAMPLE 23

(+)-7-Fluoro-1-methyl-4-oxo-8-(3-phenyl-1-piperazinyl)-1,4-dihydrobenzo[b][1,8]naphthyridine-3-carboxylic acid was prepared in the same manner as (RS)-7-fluoro-1-methyl-4-oxo-8-(3-phenyl-1-piperazinyl)-1,4-dihydrobenzo[b][1,8]naphthyridine-3-carboxylic acid (Example 19), starting with 3-ethoxycarbonyl-7,8-difluoro-1-methyl-4-oxo-1,4-dihydrobenzo[b][1,8]naphthyridine (4.4 g), (−)-2-phenylpiperazine (2.7 g) ($[\alpha]_D^{20} = -37° \pm 0.5$ (c=2; ethanol)) and sodium carbonate (1.48 g). A yellow solid (6.3 g), m.p. 226° C., is obtained. After acid hydrolysis under the same conditions as those described in Example 12 for (RS)-3-ethoxycarbonyl-7-fluoro-1-methyl-4-oxo-8-(3-phenyl-1-piperazinyl)-1,4-dihydrobenzo[b][1,8]naphthyridine, (+)-7-fluoro-1-methyl-4-oxo-8-(3-phenyl-1-piperazinyl)-1,4-dihydrobenzo[b][1,8]naphthyridine-3-carboxylic acid (R) isomer (4.26 g) is obtained in the form of a yellow solid, m.p. 276°-278° C.

$[\alpha]_D^{20} = +40.6° \pm 1$ (c=1; acetic acid).

EXAMPLE 24

A suspension of (RS)-3-ethoxycarbonyl-7,9-difluoro-1-methyl-4-oxo-8-(3-phenyl-1-piperazinyl)-1,4-dihydrobenzo[b][1,8]naphthyridine (2 g) in ethanol (25 cc) and N aqueous potassium hydroxide (15 cc) is heated with stirring to a temperature in the region of 75° C. for 2 hours. The solution obtained, at approximately 75° C., is treated with 10% strength aqueous acetic acid solution (9 g). The insoluble matter obtained is drained at a temperature in the region of 75° C. and washed with water (3×30 cc) at approximately 20° C. After 1 recrystallization in dimethylformamide (40 cc), (RS)-7,9-difluoro-1-methyl-4-oxo-8-(3-phenyl-1-piperazinyl)-1,4- dihydrobenzo[b][1,8]naphthyridine-3-carboxylic acid (1.5 g) is obtained in the form of an orange-colored solid, m.p. 298° C.

(RS)-3-Ethoxycarbonyl-7,9-difluoro-1-methyl-4-oxo-8-(3-phenyl-1-piperazinyl)-1,4-dihydrobenzo[b][1,8-]naphthyridine is prepared in the following manner:

A suspension of 3-ethoxycarbonyl-7,8,9-trifluoro-1-methyl-4-oxo-1,4-dihydrobenzo[b][1,8]naphthyridine (1.8 g) and (RS)-2-phenylpiperazine (3.2 g) in dimethyl sulphoxide (30 cc) is heated to a temperature in the region of 100° C. with stirring for 1 hour and a half. The solution obtained, at approximately 100° C., is poured with stirring into a mixture of water (150 cc) and ice (50 g). The suspension obtained is extracted at approximately 20° C. with trichloromethane (3×40 cc). The combined organic extracts are washed with water (2×50 cc), dried over magnesium sulphate, filtered and concentrated to dryness under reduced pressure (20 kPa) at approximately 50° C. The solid obtained is recrystallized in a mixture of dimethylformamide (40 cc) and ethanol (40 cc). (RS)-3-Ethoxycarbonyl-7,9-difluoro-1-methyl-4-oxo-8-(3-phenyl-1-piperazinyl)-1,4-dihydrobenzo[b][1,8]naphthyridine (2 g) is obtained in the form of a yellow solid, m.p. 216° C.

3-Ethoxycarbonyl-7,8,9-trifluoro-1-methyl-4-oxo-1,4-dihydrobenzo[b][1,8]naphthyridine is prepared in the following manner:

A solution of approximately 5° C. of methylamine (10 g) in ethanol (50 cc) is added in the course of 10 minutes at between 5° and 10° C. to a suspension, maintained at a temperature in the region of 5° C., of ethyl 2-(2-chloro-6,7,8-trifluoro-3-quinolinecarbonyl)-3-(dimethylamino)acrylate (19.3 g) in ethanol (150 cc), the mixture is stirred for 1 hour at between 5° and 10° C. and the temperature is allowed to rise to approximately 20° C. The solution obtained is treated with DBU (7.6 g) and heated to approximately 30° C. for 1 hour. After cooling to a temperature in the region of 20° C., the product is drained and washed with ethanol (2×100 cc) and isopropyl ether (2×100 cc). 3-Ethoxycarbonyl-7,8,9-trifluoro-1-methyl-4-oxo-1,4-dihydrobenzo[b][1,8-]naphthyridine (13.4 g) is obtained in the form of a yellow solid, m.p. 320° C., which is used without further purification for the subsequent steps.

Ethyl 2-(2-chloro-6,7,8-trifluoro-3-quinolinecarbonyl)-3-(dimethylamino)acrylate may be prepared in the following manner:

A suspension of ethyl 3-(2-chloro-6,7,8-trifluoro-3-quinolyl)-3-oxopropionate (26.7 g) in ethyl acetate (270 cc) and N,N-dimethylformamide dimethyl acetal (32 cc) is heated to a temperature in the region of 75° C. with stirring for 2 hours. The reaction mixture is concentrated to dryness under reduced pressure (20 kPa) at approximately 50° C. The dry extract is taken up with isopropyl ether (175 cc), drained and washed with the same solvent (2×85 cc). Ethyl 2-(2-chloro-6,7,8-trifluoro-3-quinolinecarbonyl)-3-(dimethylamino)acrylate (19.32 g) is obtained in the form of an orange-colored solid, m.p. 118° C., which is used without further purification for the subsequent steps.

Ethyl 3-(2-chloro-6,7,8-trifluoro-3-quinolyl)-3-oxopropionate is prepared in the following manner:

A suspension of 2-chloro-6,7,8-trifluoro-3-quinolinecarboxylic acid (46.3 g) in trichloromethane (640 cc) and thionyl chloride (84 cc) is heated with stirring to a temperature in the region of 60° C. for 6 hours. The solution obtained is concentrated to dryness under reduced pressure (20 kP) at approximately 50° C. The dry extract obtained is taken up with petroleum ether (40-60) (140 cc), drained and washed with the same solvent (2×60 cc). The yellow solid (47.61 g) obtained is dissolved in tetrahydrofuran (400 cc). This solution is introduced dropwise, with stirring, in the course of 1 hour and a half and at between 5° C. and 10° C. into a solution (250 cc) of magnesium chelate of ethyl monomalonate in tetrahydrofuran, prepared under the conditions of Example 19. The temperature is allowed to rise to approximately 20° C. and the mixture is stirred for a further 2 hours under these conditions. The solution obtained is introduced dropwise, with vigorous stirring, in the course of 1 hour and at a temperature in the region of 5° C. into 0.5N sulphuric acid (1750 cc). The mixture is stirred for a further 2 hours at this temperature and the product is extracted at approximately 5° C. with ethyl ether (3×600 cc). The combined organic phases are washed with water (3×500 cc), dried over magnesium sulphate and concentrated under reduced pressure (20 kPa) at a temperature in the region of 30° C. The dry extract is taken up with a mixture of isopropyl ether (135 cc) and n-hexane (15 cc), drained at approximately 5° C. and washed with the same mixture (2×115 cc) at the same temperature. Ethyl 3-(2-chloro-6,7,8-trifluoro-3-quinolyl)-3-oxopropionate (47.4 g) is obtained in the form of a beige solid, m.p. 78°–80° C., which is used without further purification for the subsequent steps.

2-Chloro-6,7,8-trifluoro-3-quinolinecarboxylic acid is prepared in the following manner:

A solution of potassium permanganate (69.65 g) in water (730 cc) is added in the course of 1 hour to a stirred suspension, cooled to approximately 10° C., of 2-chloro-6,7,8-trifluoro-3-formyl-1,4-dihydroquinoline (45.7 g) in N potassium hydroxide (585 cc), while the temperature is maintained at between 10° and 14° C. The mixture is left stirring for a further 30 minutes at approximately 10° C. Sodium dithionite (12 g) is added and the mixture is stirred for 10 minutes at a temperature in the region of 10° C., filtered through diatomaceous silica and washed with water (3×400 cc). The filtrate and washings are combined and treated with 35% strength aqueous hydrochloric acid solution (70 cc). The precipitate formed is extracted with ethyl acetate (3×500 cc). The combined organic extracts are dried over magnesium sulphate, filtered and concentrated under reduced pressure (20 kPa) at 50° C. The residue is taken up with a mixture of ethyl ether (100 cc) and isopropyl ether (100 cc), drained and washed with the same mixture (100 cc). 2-Chloro-6,7,8-trifluoro-3-quinolinecarboxylic acid (46.43 g) is obtained in the form of a colorless solid, decomposing at 225°–230° C., which is used without further purification for the subsequent steps.

2-Chloro-6,7,8-trifluoro-3-formyl-1,4-dihydroquinoline is prepared in the following manner:

Phosphoryl chloride (50 cc) is added in the course of 40 minutes with stirring at between 5° and 10° C. to a mixture of trichloromethane (525 cc) and dimethylformamide (49 cc), the mixture is stirred for 15 minutes at this temperature and the temperature is allowed to rise to approximately 20° C. To the solution obtained, 6,7,8-trifluoro-3,4-dihydrocarbostyril (46.8 g) is added gradually in the course of 20 minutes at approximately 20° C. with vigorous stirring. The mixture is left stirring for 30 minutes at a temperature in the region of 20° C., heated to approximately 60° C. and maintained at the same temperature for 2 hours and a half. The reaction mixture is concentrated under reduced pressure (20 kPa) at approximately 50° C. The oily residue is poured with vigorous stirring into ice (500 g). Sodium acetate (100 g) is added in small portions in the course of 30 minutes. The suspension obtained is poured in the course of 15 minutes with vigorous stirring into water (1 liter) heated beforehand to approximately 90° C., and the mixture is stirred for a further 15 minutes at the same temperature. The insoluble matter is drained at approximately 90° C. and washed with water (3×250 cc). 2-Chloro-6,7,8-trifluoro-3-formyl-1,4-dihydroquinoline (47.7 g) is obtained in the form of a colorless solid, decomposing at 220° C.

6,7,8-Trifluoro-3,4-dihydrocarbostyril is prepared in the following manner:

6,7,8-Trifluorocarbostyril (24.35 g), suspended in a mixture of ethanol (450 cc) and dimethylformamide (150 cc), is hydrogenated with stirring at approximately 50° C. in the presence of Raney nickel (5 g) under a pressure of 1 atmosphere, until the absorption of hydrogen is complete. The Raney nickel used, of W-2 grade, is washed beforehand with 2% aqueous acetic acid solution (50 cc), with water (2×50 cc) and with ethanol (3×50 cc). The reaction mixture is treated with dimethylformamide (250 cc) and filtered at approximately 50° C. through diatomaceous silica. The filtrate is concentrated under reduced pressure (20 kPa) at approximately 70° C. The dry extract is taken up with water (150 cc), drained and washed with water (2×50 cc). 6,7,8-Trifluoro-3,4-dihydrocarbostyril (23.6 g) is obtained in the form of a light beige solid, m.p. 217° C., which is used without further purification for the subsequent steps.

6,7,8-Trifluorocarbostyril is prepared in the following manner:

4-Chloro-6,7,8-trifluorocarbostyril (60.83 g), suspended in acetic acid (520 cc) and triethylamine (38.15 cc), is hydrogenated under a pressure of 1 atmosphere at a temperature in the region of 25° C. in the presence of palladium on charcoal (5.25 g; 10% Pd) until the absorption of hydrogen is complete. The reaction mixture is then heated to approximately 40° C. and filtered at the same temperature through diatomaceous silica for filtration. The filtrate is concentrated under reduced pressure (20 kPa) at a temperature in the region of 50° C. The dry extract is taken up with water (400 cc); the insoluble matter is drained and washed with water (4×170 cc), ethanol (2×110 cc) and isopropyl ether (2×100 cc). 6,7,8-Trifluorocarbostyril (48.35 g) is obtained in the form of a colorless solid, subliming at 288° C., which is used without further purification for the subsequent steps.

4-Chloro-6,7,8-trifluorocarbostyril is prepared in the following manner:

A suspension of 4-chloro-2-ethoxy-6,7,8-trifluoroquinoline (70.4 g) in 35% strength aqueous hydrochloric acid solution (170 cc), acetic acid (420 cc) and water (250 cc) is heated with stirring to a temperature in the region of 100° C. for 2 hours and a half. After cooling to approximately 20° C., the reaction mixture is poured into water (1100 cc) at approximately 5° C. and stirred for 15 minutes at this temperature and the insoluble matter is then drained and washed with water (3×220 cc). 4-Chloro-6,7,8-trifluorocarbostyril (61 g) is obtained in the form of a cream-colored solid, m.p. 213° C., which is used without further purification for the subsequent steps.

4-Chloro-2-ethoxy-6,7,8-trifluoroquinoline is prepared in the following manner:

A suspension of 2-ethoxy-6,7,8-trifluoro-4-hydroxyquinoline (69.5 g) is phosphoryl chloride (430 cc) is heated with stirring to a temperature in the region of 100° C. for 30 minutes. The solution obtained is concentrated under reduced pressure (20 kPa) at approximately 60° C. to a volume of 100 cc. The residue is taken up with ethyl acetate (750 cc); the solution obtained is poured with stirring in the course of 10 minutes into a mixture of water (400 cc) and ice (200 g), and left stirring under these conditions for 30 minutes. After separation of the organic extract, the aqueous phase is again extracted with ethyl acetate (2×250 cc). The combined organic extracts are washed with water (3×250 cc), dried over magnesium sulphate and concentrated under reduced pressure (20 kPa) at approximately 40° C. The oily residue obtained is taken up with petroleum ether (40-60) (370 cc). After filtration through diatomaceous silica, the filtrate is concentrated to dryness under reduced pressure (20 kPa) at approximately 30° C. 4-Chloro-2-ethoxy-6,7,8-trifluoroquinoline (70.7 g) is obtained in the form of a beige solid, m.p. 45° C., which is used without further purification for the subsequent steps.

2-Ethoxy-6,7,8-trifluoro-4-hydroxyquinoline may be prepared in the following manner:

A solution of 2,3,4-trifluoro-N-[1-ethoxy-2-(ethoxycarbonyl)ethylidene]aniline (122 g) in phenyl ether (120 cc) is introduced dropwise in the course of 25 minutes and with stirring into phenyl ether (600 cc) at a temperature in the region of 250° C. while the ethanol formed is removed by distillation. After stirring for 15 minutes at the same temperature, the solution is cooled to approximately 20° C. and treated with n-hexane (750 cc). The precipitate formed is drained and washed with n-hexane (3×200 cc). 2-Ethoxy-6,7,8-trifluoro-4-hydroxyquinoline (69.5 g) is obtained in the form of a beige solid, m.p. 171° C., which is used without further purification for the subsequent steps.

2,3,4-Trifluoro-N-[1-ethoxy-2-(ethoxycarbonyl)ethylidene]aniline may be prepared in the following manner:

2,3,4-Trifluoroaniline (58.8 g) is added in a single portion with stirring to a solution of 2-ethoxycarbonyl-1-ethoxyethylideneamine hydrochloride (90 g) in ethanol (820 cc). After 48 hours' stirring at a temperature in the region of 20° C., the suspension obtained is filtered; the filtrate is concentrated under reduced pressure (20 kPa) at a temperature in the region of 50° C. The oily residue is taken up with water (250 cc). The mixture obtained is extracted with ethyl ether (3×200 cc). The combined organic extracts are washed with water (4×150 cc), dried over magnesium sulphate and concentrated under reduced pressure (20 kPa) at approximately 30° C. 2,3,4-Trifluoro-N-[1-ethoxy-2-(ethoxycarbonyl)ethylidene]aniline (122 g) is obtained in the form of a yellow oil, which is used without further purification for the subsequent steps.

2-Ethoxycarbonyl-1-ethoxyethylideneamine was prepared according to the method described by A. Pinner et al., Ber. Dtsch. Chem. Ges., 28, 478 (1895).

EXAMPLE 25

Working under the conditions of Example 39, but starting with (R)-3-ethoxycarbonyl-7,9-difluoro-1-methyl-4-oxo-8-(3-phenyl-1-piperazinyl)-1,4-dihydrobenzo[b][1,8]naphthyridine (0.978 g), and after 1 recrystallization in dimethylformamide (25 cc), (R)-7,9-difluoro-1-methyl-4-oxo-8-(3-phenyl-1-piperazinyl)-1,4-dihydrobenzo[b][1,8]naphthyridine-3-carboxylic acid (0.540 g) is obtained in the form of a yellow solid, decomposing at 270°-272° C.

$[\alpha]_D^{20} = +113° \pm 5$ (c=2; trichloromethane).

Working under the conditions of Example 39, but starting with 3-ethoxycarbonyl-7,8,9-trifluoro-1-methyl-4-oxo-1,4-dihydrobenzo[b][1,8]naphthyridine (1.21 g) and (R)-2-phenylpiperazine (0.7 g), and after recrystallization in ethanol (22 cc) containing dimethylformamide (30%), (R)-3-ethoxycarbonyl-7,9-difluoro-1-methyl-4-oxo-8-(3-phenyl-1-piperazinyl)-1,4-dihydrobenzo[b][1,8]naphthyridine (1.02 g) is obtained in the form of a yellow solid, m.p. 216° C.

$[\alpha]_D^{22} = +98° \pm 2$ (c=0.5; acetic acid).

EXAMPLE 26

Working under the conditions of Example 25, but starting with (S)-3-ethoxycarbonyl-7,9-difluoro-1-methyl-4-oxo-8-(3-phenyl-1-piperazinyl)-1,4-dihydrobenzo[b][1,8]naphthyridine (1.33 g), (S)-7,9-difluoro-1-methyl-4-oxo-8-(3-phenyl-1-piperazinyl)-1,4-dihydrobenzo[b][1,8]naphthyridine-3-carboxylic acid (0.779 g) is obtained in the form of a yellow solid, decomposing at 270°-272° C.

$[\alpha]_D^{20} = +118° \pm 5$ (c=0.2; trichloromethane).

Working under the conditions of Example 26, but starting with 3-ethoxycarbonyl-7,8,9-trifluoro-1-methyl-4-oxo-1,4-dihydrobenzo[b][1,8]naphthyridine (1.38 g) and (S)-2-phenylpiperazine (0.8 g), (S)-3-ethoxycarbonyl-7,9-difluoro-1-methyl-4-oxo-8-(3-phenyl-1-piperazinyl)-1,4-dihydrobenzo[b][1,8]naphthyridine (1.02 g) is obtained in the form of a yellow solid, m.p. 216° C.

$[\alpha]_D^{20} = -99° \pm 2$ (c=0.5; acetic acid).

EXAMPLE 27

(RS)-1-Cyclopropyl-7,9-difluoro-4-oxo-8-(3-phenyl-1-piperazinyl)-1,4-dihydrobenzo[b][1,8]-naphthyridine-3-carboxylic acid was prepared under the conditions of Example 24, but starting with (RS)-1-cyclopropyl-3-ethoxycarbonyl-7,9-difluoro-4-oxo-8-(3-phenyl-1-piperazinyl)-1,4-dihydrobenzo[b][1,8]naphthyridine (1.8 g). After one recrystallization in a mixture of dimethylformamide (30 cc) and ethanol (20 cc), (RS)-1-cyclopropyl-7,9-difluoro-4-oxo-8-(3-phenyl-1-piperazinyl)-1,4-dihydrobenzo [1,8]naphthyridine-3-carboxylic acid (1.2 g) is obtained in the form of a yellow solid, m.p. 274° C.

(RS)-1-Cyclopropyl-3-ethoxycarbonyl-7,9-difluoro-4-oxo-8-(3-phenyl-1-piperazinyl)-1,4-dihydrobenzo[b][1,8]naphthyridine was prepared under the conditions of Example 19, but starting with 1-cyclopropyl-3-ethoxycarbonyl-7,8,9-trifluoro-4-oxo-1,4-dihydrobenzo[b][1,8]naphthyridine (1.8 g) and (RS)-2-phenylpiperazine (3.2 g). After recrystallization in a mixture of dimethylformamide (5 cc) and ethanol (40 cc), (RS)-1-cyclopropyl-3-ethoxycarbonyl-7,9-difluoro-4-oxo-8-(3-phenyl-1-piperazinyl)-1,4-dihydrobenzo[b][1,8]naphthyridine (1.8 g) is obtained in the form of a yellow solid, m.p. 242° C.

1-Cyclopropyl-3-ethoxycarbonyl-7,8,9-trifluoro-4-oxo-1,4-dihydrobenzo[b][1,8]naphthyridine may be prepared under the following conditions:

Cyclopropylamine (4.12 g) is added in the course of 5 minutes to a solution, maintained at a temperature in the region of 20° C., of ethyl 2-(2-chloro-6,7,8-trifluoro-3-quinolinecarbonyl)-3-(dimethylamino)acrylate (7 g) in trichloromethane (100 cc), and the mixture is stirred for a further 4 hours at the same temperature. The reaction mixture is concentrated under reduced pressure (20 kPa) at approximately 50° C. The oily residue obtained is taken up with ethanol (100 cc) and DBU (3 g). The mixture is heated to 80° C. and kept stirring at the same temperature for 1 hour and a half. After cooling to approximately 20° C., the insoluble matter is drained and washed with ethanol (2×30 cc) and isopropyl ether (2×30 cc). 1-Cyclopropyl-3-ethoxycarbonyl-7,8,9-trifluoro-4-oxo-1,4-dihydrobenzo[b][1,8]naphthyridine (4.5 g) is obtained in the form of a colorless solid, m.p. 260° C.

EXAMPLE 28

Working under the conditions of Example 39, but starting with (RS)-3-ethoxycarbonyl-7,9-difluoro-1-(2-fluoroethyl)-4-oxo-8-(3-phenyl-1-piperazinyl)-1,4-dihydrobenzo[b][1,8]naphthyridine (2.4 g), (RS)-7,9-difluoro-1-(2-fluoroethyl)-4-oxo-8-(3-phenyl-1-piperazinyl)-1,4-dihydrobenzo[b][1,8]naphthyridine-3-carboxylic acid (1.6 g) is obtained in the form of a yellow solid, decomposing at 307°-310° C.

(RS)-3-Ethoxycarbonyl-7,9-difluoro-1-(2-fluoroethyl)-4-oxo-8-(3-phenyl-1-piperazinyl)-1,4-dihydrobenzo[b][1,8]naphthyridine was prepared under the following conditions: a suspension of 3-ethoxycarbonyl-1-(2-fluoroethyl)-7,8,9-trifluoro-4-oxo-1,4-dihydrobenzo[b][1,8]naphthyridine (2.8 g), (RS)-2-phenylpiperazine (1.7 g) and sodium carbonate (1.1 g) in dimethyl sulphoxide (40 cc) is heated with stirring to a temperature in the region of 100° C. for 2 hours. After cooling to approximately 20° C., the reaction mixture is poured into water (200 cc) and extracted with trichloromethane (3×100 cc). The combined organic extracts are washed with water (1×50 cc) and concentrated under reduced pressure (20 kPa) at a temperature in the region of 40° C. The oily residue is taken up with ethanol (100 cc) and concentrated again under reduced pressure under the above conditions. The solid obtained is recrystallized in ethanol (100 cc) containing dimethylformamide (20%), drained and washed with ethanol (2×20 cc). The expected product (2.4 g) is obtained in the form of a yellow solid, m.p. 208° C.

3-Ethoxycarbonyl-1-(2-fluoroethyl)-7,8,9-trifluoro-4-oxo-1,4-dihydrobenzo[b][1,8]naphthyridine was prepared under conditions similar to Example 3, but starting with ethyl 2-(2-chloro-6,7,8-trifluoro-3-quinolinecarbonyl)(dimethylamino)acrylate (3.9 g), 2-fluoroethylamine hydrochloride (3 g) and triethylamine (4.2 cc) in ethanol (100 cc). After the addition of DBU (1.8 cc), the solution is heated for 2 hours to 80° C. After the same treatment of the reaction mixture as in Example 24, 3-ethoxycarbonyl-7,8,9-trifluoro-1-(2-fluoroethyl)-4-oxo-1,4-dihydrobenzo[b][1,8]naphthyridine (2.8 g) is obtained in the form of a yellow solid, m.p. 302°-304° C.

Ethyl 2-(2-chloro-6,7,8-trifluoro-3-quinolinecarbonyl) (dimethylamino)acrylate may be prepared as described in Example 24.

EXAMPLE 29

A suspension of (RS)-8-(3-benzyl-1-piperazinyl)-3-ethoxycarbonyl-7-fluoro-1-methyl-4-oxo-1,4dihydrobenzo[b][1,8]naphthyridine (2.65 g) in N aqueous potassium hydroxide (14 cc) and ethanol (20 cc) is heat ° to a temperature in the region of 80° C. for 20 minutes, treated at the same temperature with 5% strength acetic acid (32 cc) and stirred for 20 minutes. The insoluble matter is drained at approximately 80° C. and washed with water (2×20 cc), ethanol (2×20 cc) and ethyl ether (2×20 cc). After 2 recrystallizations in dimethylformamide (50 cc each time), (RS)-8-(3-benzyl-1-piperazinyl)-7-fluoro-1-methyl-4-oxo-1,4-dihydrobenzo[b][1,8]naphthyridine-3-carboxylic acid (2.05 g) is obtained in the form of a yellow solid, decomposing at 270°-275° C.

(RS)-8-(3-Benzyl-1-piperazinyl)-3-ethoxycarbonyl-7-fluoro-1-methyl-4-oxo-1,4-dihydrobenzo [b][1,8]naphthyridine is prepared in the following manner;

A suspension of 3-ethoxycarbonyl-7,8-difluoro-1-methyl-4-oxo-1,4-dihydrobenzo[b][1,8]naphthyridine (1.3 g) and (RS)-2-benzylpiperazine (1.3 g) in dimethyl sulphoxide (25 cc) is heated to approximately 90° C. with stirring for 1 hour 45 minutes. After cooling to a temperature in the region of 20° C., the reaction mixture is treated with water (100 cc) and extracted with trichloromethane (3×30 cc). The combined organic extracts are washed with water (3×30 cc), dried over magnesium sulphate, filtered and concentrated to dryness at approximately 50° C. under reduced pressure (20 kPa). After 1 recrystallization in a mixture of dimethylformamide (4 cc) and ethanol (1 cc), (RS)-8-(3-benzyl-1-piperazinyl)-3-ethoxycarbonyl-7-fluoro-1-methyl-4-oxo-1,4-dihydrobenzo[b][1,8]naphthyridine (1.6 g) is obtained in the form of a yellow solid, m.p. 190° C.

(RS)-2-Benzylpiperazine may be prepared by the hydrogenation of 2-benzylpiperazine, obtained according to the method described by J. D. BEHUN and R. LEVINE, J. Org. Chem., 26, 3379, (1961).

A solution of 2-benzylpyrazine (8 g) in acetic acid (60 cc) is treated with platinum dioxide (0.8 g) and hydrogenated under a pressure of 1 atmosphere at approximately 20° C. When the absorption of hydrogen is complete, the catalyst is removed by filtration through diatomaceous silica. The solution is concentrated to dryness under reduced pressure (20 kPa) at approximately 60° C. The dry extract is suspended in ethanol (40 cc) and treated at approximately 20° C. with a solution of sodium ethylate prepared from sodium (1.49 g) in ethanol (40 cc). After 2 hours' stirring at approximately 20° C., the suspension is concentrated to dryness under reduced pressure (20 kPa) at approximately 30° C. The dry extract is taken up with ethyl ether (60 cc). The insoluble matter is removed by filtration through diatomaceous silica. The filtrate is concentrated to dryness under reduced pressure under the same conditions as above. The dry extract is taken up with isopropyl ether (20 cc), drained and washed with the same solvent (2×5 cc). (RS)-2-Benzylpiperazine (5.32 g) is obtained in the form of a light beige solid, m.p. 90° C.

EXAMPLE 30

Working under the conditions of Example 39, but starting with (RS)-3-ethoxycarbonyl-7-fluoro-8-[3-(2-fluorophenyl)-1-piperazinyl]-1-methyl-4-oxo-1,4-dihydrobenzo[b][1,8]naphthyridine (1.3 g), (RS)-7-fluoro-8-[3-(2-fluorophenyl)-1-piperazinyl]-1-methyl-4-oxo-1,4-dihydrobenzo[b][1,8]naphthyridine-3-carboxylic acid (0.97 g) is obtained in the form of a yellow solid, m.p. 264° C.

(RS)-3-Ethoxycarbonyl-7-fluoro-8-[3-(2-fluorophenyl)-1-piperazinyl]-1-methyl-4-oxo-1,4-dihydrobenzo[b][1,8]naphthyridine was prepared under the conditions of Example 39, but starting with 3-ethoxycarbonyl-7,8-difluoro-1-methyl-4-oxo-1,4-dihydrobenzo[b][1,8]naphthyridine (1.59 g) and (RS)-2-(2-fluorophenyl)piperazine (1.08 g). After recrystallization in dimethylformamide (60 cc) containing ethanol (50%), the expected product (1.3 g) is obtained in the form of a yellow solid, m.p. 228° C.

EXAMPLE 31

(RS)-7,9-Difluoro-8-[3-(4-fluorophenyl)-1-piperazinyl]-1-methyl-4-oxo-1,4-dihydrobenzo[b][1,8]naphthyridine-3-carboxylic acid was prepared under the conditions of Example 24, but starting with (RS)-3-ethoxycarbonyl-7,9-difluoro-8-[3-(4-fluorophenyl)-1-piperazinyl]-1-methyl-4-oxo-1,4-dihydrobenzo[b][1,8]naphthyridine (1.5 g). After recrystallization in dimethylformamide (30 cc), (RS)-7,9-difluoro-8-[3-(4-fluorophenyl)-1-piperazinyl]-1-methyl-4-oxo-1,4-dihydrobenzo[b][1,8]naphthyridine-3-carboxylic acid (1 ) is obtained in the form of a yellow solid, m.p. 266° C.

(RS)-3-Ethoxycarbonyl-7,9-difluoro-8-[3-(4-fluorophenyl)-1-piperazinyl]-1-methyl-4-oxo-1,4-dihydrobenzo[9 [1,8]naphthyridine was prepared under the conditions of Example 39, but starting with 3-ethoxycarbonyl-7,8,9-trifluoro-1-methyl-4-oxo-1,4-dihydrobenzo[b][1,8]naphthyridine (2 g) and (RS)-2-(4-fluorophenyl)piperazine (4 g). After 1 recrystallization in a mixture of dimethylformamide (3.5 cc) and ethanol (31.5 cc), (RS)-3-ethoxycarbonyl-7,9-difluoro-8-[3-(4-fluorophenyl)-1-piperazinyl]-1-methyl-4-oxo-1,4-dihydrobenzo[b][1,8]naphthyridine (2.1 g) is obtained in the form of a beige solid, m.p. 242° C.

EXAMPLE 32

(RS)-1-Ethyl-7-fluoro-8-[3-(4-methoxyphenyl)-1-piperazinyl]-4-oxo-1,4-dihydrobenzo [b][1,8]naphthyridine-3-carboxylic acid was prepared under the conditions described below in Example 33, but starting with (RS)-3-ethoxycarbonyl-1-ethyl-7-fluoro-8-[3-(4-methoxyphenyl)-1-piperazinyl]-4-oxo-1,4-dihydrobenzo[b][1,8]naphthyridine (1.5 g). After recrystallization in dimethylformamide (30 cc), (RS)-1-ethyl-7-fluoro-8-[3-(4-methoxyphenyl)-1-piperazinyl]-4-oxo-1,4-dihydrobenzo[b][1,8]naphthyridine-3-carboxylic acid (0.85 g) is obtained in the form of a yellow solid, m.p. 270° C.

(RS)-3-Ethoxycarbonyl-1-ethyl-7-fluoro-8-[3-(4-methoxyphenyl)-1-piperazinyl]-4-oxo-1,4-dihydrobenzo[b][1,8]naphthyridine was prepared under the conditions of Example 33, but starting with 3-ethoxycarbonyl-1-ethyl-7,8-difluoro-4-oxo-1,4-dihydrobenzo [b][1,8]naphthyridine (1.99 g) and (RS)-2-(4-methoxyphenyl)piperazine (2.3 g). (RS)-3-Ethoxycarbonyl-1-ethyl-7-fluoro-8-[3-(4-methoxyphenyl)-1-piperazinyl]-4-oxo-1,4-dihydrobenzo[b][1,8]naphthyridine (2.2 g) is obtained in the form of a beige solid, m.p. 210°-212° c.

3-Ethoxycarbonyl-1-ethyl-7,8-difluoro-4-oxo-1,4-dihydrobenzo[b][1,8]naphthyridine was prepared under the following conditions:

A solution at approximately 2° C. of ethylamine (14.6 g) in ethanol (200 cc) is added in the course of 10 minutes at between 2° and 5° C. and with stirring to a suspension of ethyl 2-(2-chloro-6,7-difluoro-3-quinolinecarbonyl)-3-(dimethylamino)acrylate (20 g) in ethanol (200 cc) at approximately 2° C., the mixture is stirred for a further 40 minutes at between 2° and 5° C. and the temperature is then allowed to rise to approximately 20° C. in the course of 2 hours. After 24 hours at approximately 20° C., the insoluble matter is drained and washed with ethano  ×30 cc) and isopropyl ether (2×50 cc). 3-Ethoxycarbonyl-1-ethyl-7,8-difluoro-4-oxo-1,4-dihydrobenzo [b][1,8]naphthyridine (16.35 g) is obtained in the form of a beige solid, m.p. 290° C.

EXAMPLE 33

(RS)-1-Cyclopropyl-7-fluoro-8-[3-(4-methoxyphenyl)-1-piperazinyl]-4-oxo-1,4-dihydrobenzo [b][1,8]naphthyridine-3-carboxylic acid was prepared under the conditions of Example 29, but starting with (RS)-1-cyclopropyl-3-ethoxycarbonyl-7-fluoro-8-[3-(4-methoxyphenyl)-1-piperazinyl]-4-oxo-1,4-dihydrobenzo[b][1,8]naphthyridine (1.5 g) in N aqueous potassium hydroxide (18.4 cc) and ethanol (18.4 cc). After 1 recrystallization in dimethylformamide (50 cc), (RS)-1-cyclopropyl-7-fluoro-8-[3-(4-methoxyphenyl)-1-piperazinyl]-4-oxo-1,4-dihydrobenzo [b][1,8]naphthyridine-3-carboxylic acid (1.5 g) is obtained in the form of a yellow solid, decomposing at 287° C.

(RS)-1-Cyclopropyl-3-ethoxycarbonyl-7-fluoro8-[3-(4-methoxyphenyl)-1-piperazinyl]-4-oxo-1,4-dihydrobenzo[b][1,8]naphthyridine was prepared in the following manner:

A suspension of 1-cyclopropyl-3-ethoxycarbonyl-7,8-difluoro-4-oxo-1,4-dihydrobenzo[b][1,8]naphthyridine (2 g) and (RS)-3-(4-methoxyphenyl)piperazine (2.3 g) in dimethyl sulphoxide (20 cc) is heated to a temperature in the region of 90° C. for 1 hour and a half. After cooling to approximately 20° C., the insoluble matter is drained, washed with water (3×15 cc) and recrystallized in a mixture of ethanol (100 cc) and dimethylformamide (25 cc). (RS)-1-Cyclopropyl-3-ethoxycarbonyl-7-fluoro-8-[3-(4-methoxyphenyl)-1-piperazinyl]-4-oxo-1,4-dihydrobenzo[b][1,8]naphthyridine (2.1 g) is obtained in the form of a yellow solid, m.p. 199° C.

1-Cyclopropyl-3-ethoxycarbonyl-7,8-difluoro-4-oxo-1,4-dihydrobenzo[b][1,8]naphthyridine was prepared in the following manner:

A solution of ethyl 2-(2-chloro-6,7-difluoro-3-quinolinecarbonyl)-3-(dimethylamino)acrylate (20 g) and cyclopropylamine (9.25 g) in trichloromethane (80 cc) is stirred at a temperature in the region of 20° C. for 5 hours. The solution is concentrated under reduced pressure (20 kPa) at approximately 40° C. The residue is taken up in ethanol (300 cc), treated with DBU (8.2 g) and heated with stirring to approximately 75° C. for 30 minutes. After cooling to approximately 20° C., the insoluble matter is drained and washed with ethanol (2×30 cc). 1-Cyclopropyl-3-ethoxycarbonyl-7,8-difluoro-4-oxo-1,4-dihydrobenzo[b][1,8]naphthyridine (11.1 g) is obtained in the form of a yellow solid, m.p. 230° C.

EXAMPLE 34

(RS)-7,9-Difluoro-8-[3-(4-methoxyphenyl)-1-piperazinyl]-1-methyl-4-oxo-1,4-dihydrobenzo [b][1,8]naphthyridine-3-carboxylic acid was prepared under conditions similar to Example 39, starting with (RS)-3-ethoxycarbonyl-7,9-difluoro-8-[3-(4-methoxyphenyl)-1-piperazinyl]-1-methyl-4-oxo-1,4-dihydrobenzo[b][1,8]naphthyridine (2.8 g) in N aqueous potassium hydroxide (24 cc) and ethanol (25 cc). (RS)-7,9-difluoro-8-[3-(4-methoxyphenyl)-1-piperazinyl]-1-methyl-4-oxo-1,4-dihydrobenzo[b][1,8]naphthyridine-3-carboxylic acid (2 g) is obtained in the form of a yellow solid, m.p. 288°-290° C.

(RS)-3-Ethoxycarbonyl-7,9-difluoro-8-[3-(4-methoxyphenyl)-1-piperazinyl]-1-methyl-4-oxo-1,4-dihydrobenzo[b][1,8]naphthyridine was prepared under the following conditions:

A suspension of 3-ethoxycarbonyl-7,8,9-trifluoro-1-methyl-4-oxo-1,4-dihydrobenzo[b][1,8]naphthyridine (2.5 g) and (RS)-2-(4-methoxyphenyl)piperazine (3.5 g) in dimethyl sulphoxide (40 cc) is heated with stirring to a temperature in the region of 95° C. for 2 hours. After treatment of the reaction mixture according to the conditions described in Example 39, (RS)-3-ethoxycarbonyl-7,9-difluoro-8-[3-(4-methoxyphenyl)-1-piperazinyl]-1-methyl-4-oxo-1,4-dihydrobenzo[b][1,8]naphthyridine (2.8 g) is obtained in the form of a yellow solid, m.p. 209° C., which is used without further purification for the subsequent steps.

3-Ethoxycarbonyl-7,8,9-trifluoro-1-methyl-4-oxo-1,4-dihydrobenzo[b][1,8]naphthyridine may be prepared as described in Example 24.

(RS)-2-(4-Methoxyphenyl)piperazine was prepared according to the method described in Example 12.

EXAMPLE 35

Working under the conditions of Example 39, but starting with (RS)-8-[3-(4-aminophenyl)-1-piperazinyl]-3-ethoxycarbonyl-7-fluoro-1-methyl-4-oxo-1,4-dihydrobenzo[b][1,8]naphthyridine (0.9 g), (RS)-8-[3-(4-aminophenyl)-1-piperazinyl]-7-fluoro-1-methyl-4-oxo-1,4-dihydrobenzo[b][1,8]naphthyridine-3-carboxylic acid (0.7 g) is obtained in the form of a yellow solid, decomposing at 315° C.

(RS)-8-[3-(4-Aminophenyl)-1-piperazinyl]-3-ethoxycarbonyl-7-fluoro-1-methyl-4-oxo-1,4 -dihydrobenzo[b][1,8]naphthyridine was prepared under the following conditions:

A suspension of (RS)-3-ethoxycarbonyl-7-fluoro-1-methyl-8-[3-(4-nitrophenyl)-1-piperazinyl]-4-oxo-1,4-dihydrobenzo[b][1,8]naphthyridine (0.7 g) and Raney nickel (5 g) in ethanol (150 cc) is hydrogenated under a pressure of 1 atmosphere at approximately 20° C. for 7 hours, which enables the theoretical quantity of hydrogen (100 cc at 20° C. and 1 atmosphere) to be absorbed. After the addition of dimethylformamide (50 cc), the catalyst is removed by filtration and the filtrate concentrated to dryness under reduced pressure (20 kPa) at approximately 50° C. The residue obtained (0.550 g) is chromatographed on silica (230–400 mesh) (15 g) suspended in chloroform containing ethanol (20%) and eluted with the same solvent mixture (200 cc). After concentration to dryness under the same conditions as above, (RS)-8-[3-(4-aminophenyl)-1-piperazinyl]-3-ethoxycarbonyl-7-fluoro-1-methyl-4-oxo-1,4-dihydrobenzo[b][1,8]naphthyridine (0.3 g) is obtained in the form of a solid, m.p. 180°-182° c.

(RS)-3-Ethoxycarbonyl-7-fluoro-1-methyl-8-[3-(4-nitrophenyl)-1-piperazinyl]-4-oxo-1,4 -dihydrobenzo[b][1,8]naphthyridine was prepared under the conditions of Example 39, but starting with 3-ethoxycarbonyl-7,8-difluoro-1-methyl-4-oxo-1,4-dihydrobenzo[b][1,8]naphthyridine (0.636 g) and (RS)-2-(4-nitrophenyl)piperazine (0.5 g). After recrystallization in dimethylformamide (10 cc), the expected product (0.7 g) is obtained in the form of a yellow solid, decomposing at approximately 300° C.

(RS)-2-(4-nitrophenyl)piperazine was prepared according to the same methods as those used in Example 8.

Starting with 4-nitrophenylglyoxal (18 g), the expected product (6.2 g) is obtained in the form of a brown oil, which was used without further purification for the subsequent steps.

Starting with 4'-nitro-5-bromoacetophenone (24.4 g), 4-nitrophenylglyoxal (9 g) is obtained in the form of a brown oil, which was used without further purification for the subsequent steps.

EXAMPLE 36

Working under the conditions of Example 39, but starting with (RS)-3-ethoxycarbonyl-7,9-difluoro-8-{3-[4-(2-hydroxyethoxy)phenyl]-1-piperazinyl}-1-methyl-4-oxo-1,4-dihydrobenzo[b][1,8]naphthyridine (2.2 g), (RS)-7,9-difluoro-8-{3-[4-(2-hydroxyethoxy)phenyl]-1-piperazinyl}-1-methyl-4-oxo-1,4-dihydrobenzo[b][1,8-]naphthyridine-3-carboxylic acid (1.6 g) is obtained in the form of a yellow solid, m.p. 226°–228° C.

(RS)-3-Ethoxycarbonyl-7,9-difluoro-8-{3-[4-(2-hydroxyethoxy)phenyl]-1-piperazinyl}-1 -methyl-4-oxo-1,4-dihydrobenzo[b][1,8]naphthyridine was prepared under the conditions of Example 39, but starting with 3-ethoxycarbonyl-7,8,9-trifluoro-1-methyl-4-oxo-1,4-dihydrobenzo[b][1,8]naphthyridine (1.9 g) and (RS)-2-[4-(2-hydroxyethoxy)phenyl]piperazine (1.6 g). The expected product (2.2 g) is obtained in the form of a yellow solid, m.p. 183° C.

3-Ethoxycarbonyl-7,8,9-trifluoro-1-methyl-4-oxo-1,4-dihydrobenzo[b][1,8]naphthyridine may be prepared as described below in Example 24.

EXAMPLE 37

Working under conditions similar to Example 39, but starting with (RS)-1-cyclopropyl-3-ethoxycarbonyl-7,9-difluoro-8-{3-[4-(2-hydroxyethoxy)phenyl]-1-piperazinyl}-4-oxo-1,4-dihydrobenzo[b][1,8]naphthyridine (2.4 g) and adding ethanol (100 cc) containing water (50%) to the reaction medium before the introduction of methanesulphonic acid, (RS)-1-cyclopropyl-7,9-difluoro-8-{3-[4-(2-hydroxyethoxy)phenyl]-1-piperazinyl}-4-oxo-1,4-dihydrobenzo[b][1,9]naphthyridine-3-carboxylic acid (1.4 g) is obtained in the form of a yellow solid, m.p. 228°–230° C.

(RS)-1-Cyclopropyl-3-ethoxycarbonyl-7,9-difluoro-8-{3-[4-(2-hydroxyethoxy)phenyl-1-piperazinyl}-4-oxo-1,4-dihydrobenzo[b][1,8]naphthyridine was prepared under the conditions of Example 39, but starting with 1-cyclopropyl-3-ethoxycarbonyl-7,8,9-trifluoro-4-oxo-1,4-dihydrobenzo[b][1,8]naphthyridine (2 g) and (RS)-2-[4-(2-hydroxyethoxy)phenylpiperazine (1.6 g). The expected product (2.4 g) is obtained in the form of a yellow solid, m.p. 225°–226° C.

1-Cyclopropyl-3-ethoxycarbonyl-7,8,9-trifluoro-4-oxo-1,4-dihydrobenzo[b][1,8]naphthyridine is prepared as described in Example 27.

(RS)-2-[4-(2-Hydroxyethoxy)phenyl]piperazine may be prepared as described in Example 16.

EXAMPLE 38

Working under the conditions of Example 39, but starting with (RS)-3-ethoxycarbonyl-7-fluoro-1-methyl-8-[3-(3,4-methylenedioxyphenyl)-1-piperazinyl]-4-oxo-1,4-dihydrobenzo[b][1,8]naphthyridine (2.1 g), after recrystallization in dimethylformamide (30 cc), (RS)-7-fluoro-1-methyl-8-[3-(3,4-methylenedioxyphenyl)-1-piperazinyl]-4-oxo-1,4-dihydrobenzo[b][1,8]naphthyridine-3-carboxylic acid (1.6 g) is obtained in the form of a yellow solid, decomposing at 255° C.

(RS)-3-Ethoxycarbonyl-7-fluoro-1-methyl-8-[3-(3,4-methylenedioxyphenyl)-1-piperazinyl]-4-oxo-1,4-dihydrobenzo[b][1,8]naphthyridine was prepared under conditions similar to Example 39, but starting with 3-ethoxycarbonyl-7,8-difluoro-1-methyl-4-oxo-1,4-dihydrobenzo[b][1,8]naphthyridine (1.59 g), (RS)-2-(3,4-methylenedioxyphenyl)piperazine (1.25 g) and sodium carbonate (0.64 g). (RS)-3-Ethoxycarbonyl-7-fluoro-1-methyl-8-[3-(3,4-methylenedioxyphenyl)-1-piperazinyl]-4-oxo-1,4-dihydrobenzo[b][1,8 naphthyridine (2.15 g) is obtained in the form of a yellow solid, m.p. 252° C.

(RS)-2-(3,4-Methylenedioxyphenyl)piperazine was prepared according to the process defined in Patent Application FR 2,351,108.

EXAMPLE 39

A suspension of (RS)-3-ethoxycarbonyl-7-fluoro-8-[3-(2-furyl)-1-piperazinyl]-1-methyl-4-oxo-1,4-dihydrobenzo[b][1,8]naphthyridine (1.3 g) in 0.5 N aqueous potassium hydroxide (12 cc) and ethanol (12 cc) is heated for 1 hour to a temperature in the region of 80° C. and then treated at the same temperature with an N aqueous solution (6 cc) of methanesulphonic acid. After cooling to approximately 20° C., the insoluble water is drained, washed with water (3×10 cc), ethanol (3×10 cc) and ethyl ether (3×10 cc) and recrystallized in a mixture of ethanol (13 cc) and dimethylformamide (27 cc). (RS)-7-Fluoro-8-[3-(2-furyl)-1-piperazinyl]-1-methyl-4-oxo-1,4-dihydrobenzo[b][1,8]naphthyridine-3-carboxylic acid (0.570 g) obtained in the form of a yellow solid, m.p. 258°–260° C.

(RS)-3-Ethoxycarbonyl-7-fluoro-8-[3-(2-furyl)-1-piperazinyl]-1-methyl-4-oxo-1,4-dihydrobenzo[b][1,8-]naphthyridine was prepared in the following manner:

A suspension of 3-ethoxycarbonyl-7,8-difluoro-1-methyl-4-oxo-1,4-dihydrobenzo[b][1,8]naphthyridine (0.96 g), (RS)-2-(2-furyl)piperazine (0.6 g) and sodium carbonate (0.38 g) in dimethyl sulphoxide (20 cc) is heated to approximately 95° C. for 5 hours and a half. After cooling to approximately 20° C., the mixture is poured into water (50 cc) at a temperature in the region of 5° C. and extracted with dichloromethane (3×100 cc). The combined organic extracts are washed with water (3×50 cc), dried over magnesium sulphate, filtered and concentrated to dryness under reduced pressure (20 kPa) at approximately 40° C. The residue obtained is taken up with ethanol (20 cc), drained and washed with ethanol (2×20 cc) and ethyl ether (3×30 cc). (RS)-3-Ethoxycarbonyl-7-fluoro-8-[3-(2-furyl)-1-piperazinyl]-1-methyl-4-oxo-1,4-dihydrobenzo[b][1,8-]naphthyridine (1.3 g) is obtained in the form of a yellow solid, m.p. 198°–200° C., which is used without further purification for the subsequent steps.

3-Ethoxycarbonyl-7,8-difluoro-1-methyl-4-oxo-1,4-dihydrobenzo[b][1,8]naphthyridine is prepared as described in Example 19.

(RS)-2-(2-Furyl)piperazine was prepared according to the process described in Patent Application EP 230,053.

EXAMPLE 40

Working under the conditions of Example 39, but starting with (RS)-1-cyclopropyl-3-ethoxycarbonyl-7-fluoro-8-[3-(2-furyl)-1-piperazinyl]-4-oxo-1,4-dihydrobenzo[b][1,8]naphthyridine (1.25 g), (RS)-1-cyclopropyl-7-fluoro-8-[3-(2-furyl)-1-piperazinyl]-4-oxo-1,4-dihydrobenzo[b][1,8]naphthyridine-3-carboxylic acid (0.95 g) is obtained in the form of a yellow solid, m.p. 240°–241° C.

(RS)-1-Cyclopropyl-3-ethoxycarbonyl-7-fluoro-8-[3-(2-furyl)-1-piperazinyl]-4-oxo-1,4-dihydrobenzo[b][1,8]naphthyridine was prepared under the conditions of Example 39, but starting with 1-cyclopropyl-7,8-difluoro-3-ethoxycarbonyl-4-oxo-1,4-dihydrobenzo[b][1,8]naphthyridine (1.05 g) and (RS)-2-(2-furyl)piperazine (0.6 g). (RS)-1-Cyclopropyl-3-ethoxycarbonyl-7-fluoro-8-[3-(2-furyl)-1-piperazinyl]-4-oxo-1,4-dihydrobenzo[b][1,8]naphthyridine (1.3 g) is obtained in the form of a yellow solid, m.p. 182° C.

1-Cyclopropyl-3-ethoxycarbonyl-7,8-difluoro-4-oxo-1,4-dihydrobenzo[b][1,8]naphthyridine was prepared in the following manner:

A solution of ethyl 2-(2-chloro-6,7-difluoro-3-quinolinecarbonyl)-3-(dimethylamino)acrylate (20 g) and cyclopropylamine (9.25 g) in trichloromethane (80 cc) is stirred at a temperature in the region of 20° C. for 5 hours. The solution is concentrated under reduced pressure (20 kPa) at approximately 40° C. The residue is taken up with ethanol (300 cc), treated with DBU (8.2 g) and heated with stirring to approximately 75° C. for 30 minutes. After cooling to approximately 20° C., the insoluble matter is drained and washed with ethanol (2×30 cc). 1-Cyclopropyl-3-ethoxycarbonyl-7,8-difluoro-4-oxo-1,4-dihydrobenzo[b][1,4]naphthyridine (11.1 g) is obtained in the form of a yellow solid, m.p. 230° C.

EXAMPLE 41

Working under the conditions of Example 39, but starting with (RS)-3-ethoxycarbonyl-7,9-difluoro-8-[3-(2-furyl)-1-piperazinyl]-1-methyl-4-oxo-4-dihydrobenzo[b][1,8]naphthyridine (1.58 g), (RS)-7,9-difluoro-8-[3-(2-furyl)-1-piperazinyl]-1-methyl-4-oxo-1,4-dihydrobenzo[b][1,8]naphthyridine-3-carboxylic acid (1.07 g) is obtained in the form of a yellow solid, m.p. 295°-296° C.

(RS)-3-Ethoxycarbonyl-7,9-difluoro-8-[3-(2-furyl)-1-piperazinyl]-1-methyl-4-oxo-1,4-dihydrobenzo[b][1,8]naphthyridine was prepared under the conditions of Example 39, but starting with 3-ethoxycarbonyl-7,8,9-trifluoro-1-methyl-4-oxo-1,4-dihydrobenzo[b][1,8]naphthyridine (1.85 g) and (RS)-2-(2-furyl)piperazine (1 g). After concentration of the combined organic extracts under reduced pressure (20 kPa, approximately 40° C.), the residual solid is recrystallized in ethanol (100 cc). (RS)-3-Ethoxycarbonyl-7,9-difluoro-8-[3-(2-furyl)-1-piperazinyl]-1-methyl-4-oxo-1,4-dihydrobenzo[b][1,8]naphthyridine (1.72 g) is obtained in the form of a yellow solid, m.p. 208°-210° C.

EXAMPLE 42

Working under the conditions of Example 39, but starting with (RS)-3-ethoxycarbonyl-7-fluoro-1-methyl-4-oxo-8-[3-(2-thienyl)-1-piperazinyl]-1,4-dihydrobenzo[b][1,8]naphthyridine (2 g), and without recrystallization, pure (RS)-7-fluoro-1-methyl-4-oxo-8-[3-(2-thienyl)-1-piperazinyl]-1,4-dihydrobenzo[b][1,8]naphthyridine-3-carboxylic acid (1.8 g) is obtained in the form of a yellow solid, m.p. 268°-270° C.

(RS)-3-Ethoxycarbonyl-7-fluoro-1-methyl-4-oxo-8-[3-(2-thienyl)-1-piperazinyl]-1,4-dihydrobenzo[b][1,8]naphthyridine was prepared under the conditions of Example 39, but starting with 3-ethoxycarbonyl-7,8-difluoro-1-methyl-4-oxo-1,4-dihydrobenzo[b][1,8]naphthyridine (1.59 g) and (RS)-2-(2-thienyl)piperazine (1.02 g). (RS)-3-Ethoxycarbonyl-7-fluoro-1-methyl-4-oxo-8-[3-(2-thienyl)-1-piperazinyl ]-1,4-dihydrobenzo[b][1,8]naphthyridine (2.25 g) is obtained in the form of a yellow solid, m.p. 228° C.

(RS)-2-(2-Thienyl)piperazine was prepared according to the conditions described by Jeffrey W. H. Watthey et al., J. Med. Chem. 26, 1116 (1983).

EXAMPLE 43

Working under the conditions of Example 39, but starting with (RS)-1-cyclopropyl-3-ethoxycarbonyl-7-fluoro-4-oxo-8-[3-(2-thienyl)-1-piperazinyl-1,4-dihydrobenzo[b][1,8]naphthyridine (2 g), (RS)-1-cyclopropyl-7-fluoro-4-oxo-8-[3-(2-thienyl)-1-piperazinyl]-1,4-dihydrobenzo[b][1,8]naphthyridine-3-carboxylic acid (1.75 g) is obtained in the form of a yellow solid, m.p. 245° C.

(RS)-1-Cyclopropyl-3-ethoxycarbonyl-7-fluoro-4-oxo-8-[3-(2-thienyl)-1-piperazinyl]-1,4-dihydrobenzo[b][1,8]naphthyridine was prepared under the conditions of Example 39, but starting with 1-cyclopropyl-7,8-difluoro-3-ethoxycarbonyl-4-oxo-1,4-dihydrobenzo[b][1,8]naphthyridine (1.7 g) and (RS)-2-(2-thienyl)piperazine (1 g). (RS)-1-Cyclopropyl-3-ethoxycarbonyl-7-fluoro-4-oxo-8-[3-(2-thienyl)-1-piperazinyl]-1,4-dihydrobenzo[b][1,8]naphthyridine (2.2 g) is obtained in the form of a yellow solid, m.p. 210°-212° C.

EXAMPLE 44

Working under the conditions of Example 39, but starting with (RS)-3-ethoxycarbonyl-7,9-difluoro-1-methyl-4-oxo-8-[3-(2-thienyl)-1-piperazinyl]-1,4-dihydrobenzo[b][1,8]naphthyridine (1.6 g), (RS)-7,9-difluoro-1-methyl-4-oxo-8-[3-(2-thienyl)-1-piperazinyl]-1,4-dihydrobenzo[b][1,8]naphthyridine-3-carboxylic acid. (0.75 g) is obtained in the form of a yellow solid, m.p. 292°-294° C.

(RS)-3-Ethoxycarbonyl-7,9-difluoro-1-methyl-4-oxo-8-[3-(2-thienyl)-1-piperazinyl]1,4-dihydrobenzo[b][1,8]naphthyridine was prepared under the conditions of Example 39, but starting with 3-ethoxycarbonyl-7,8,9-trifluoro-1-methyl-4-oxo-1,4-dihydrobenzo[b][1,8]naphthyridine (1.68 g) and (RS)-2-(2-thienyl)piperazine (1.01 g). (RS)-3-Ethoxycarbonyl-7,9-difluoro-1-methyl-4-oxo-8-[3-(2-thienyl)-1-piperazinyl]-1,4-dihydrobenzo[b][1,8]naphthyridine (1.68 g) is thereby obtained in the form of a yellow solid, m.p. 220° C.

EXAMPLE 45

Working under the conditions of Example 39, but starting with 3-ethoxycarbonyl-7-fluoro-8-(4-hydroxy-1-piperazinyl)-1-methyl-4-oxo-1,4-dihydrobenzo[b][1,8]naphthyridine (3.2 g), 7-fluoro-8-(4-hydroxy-1-piperazinyl)-1-methyl-4-oxo-1,4-dihydrobenzo[b][1,8]naphthyridine-3-carboxylic acid (2.86 g) is obtained in the form of a yellow solid, m.p. 290° C.

3-Ethoxycarbonyl-7-fluoro-8-(4-hydroxy-1-piperazinyl)-1-methyl-4-oxo-1,4-dihydrobenzo[b][1,8]naphthyridine was prepared under the conditions of Example 39, but starting with 3-ethoxycarbonyl-7,8-difluoro-1-methyl-4-oxo-1,4-dihydrobenzo[b][1,8 ]naphthyridine (3 g), 1-hydroxypiperazine dihydrochloride (1.97 g) and sodium carbonate (1.99 g). 3-Ethoxycarbonyl-7-fluoro-8-(4-hydroxy-1-piperazinyl)-1-methyl-4-oxo-1,4-dihydrobenzo[b][1,8]naphthyridine (3.25 g) is obtained in the form of a yellow solid, m.p. 258°-260° C.

1-Hydroxypiperazine dihydrochloride was prepared according to the process described by Toschio Uno et al., J. Het. Chem., 26, 393 (1988).

EXAMPLE 46

Working under the conditions of Example 39, but starting with 3-ethoxycarbonyl-7,9-difluoro-8-(4-hydroxy-1-piperazinyl)-1-methyl-4-oxo-1,4-dihydrobenzo[b][1,8]naphthyridine (1.4 g), 7,9-difluoro-8-(4-hydroxy-1-piperazinyl)-1-methyl-4-oxo-1,4-dihydrobenzo[b][1,8]naphthyridine-3-carboxylic acid (0.5 g) is obtained in the form of a yellow solid, m.p. 285°–288° C.

3-Ethoxycarbonyl-7,9-difluoro-8-(4-hydroxy-1-piperazinyl)-1-methyl-4-oxo-1,4-dihydrobenzo[b][1,8]naphthyridine was prepared under the conditions of Example 39, but starting with 3-ethoxycarbonyl-7,8,9-trifluoro-1-methyl-4-oxo-1,4-dihydrobenzo[b][1,8]naphthyridine (1.9 g), 1-hydroxypiperazine dihydrochloride (1 g) and potassium carbonate (1.6 g). 3-Ethoxycarbonyl-7,9-difluoro-8-(4-hydroxy-1-piperazinyl)-1-methyl-4-oxo-1,4-dihydrobenzo[b][1,8]naphthyridine (1.4 g) is obtained in the form of a yellow solid, m.p. 255°–258° C.

The present invention also relates to pharmaceutical compositions which are usable in human or veterinary medicine, containing, as active product, at least one produce of general formula (I) in the pure state (in free form or in salt form) or in the form of a combination with one or more compatible and pharmaceutically acceptable diluents or adjuvants. These compositions may be used orally, parenterally or rectally.

As solid compositions for oral administration, tablets, pills, powders or granules may be used. In these compositions, the active product according to the invention is mixed with one or more inert diluents or adjuvants such as sucrose, lactose or starch. These compositions can also comprise substances other than diluents, e.g. a lubricant such as magnesium stearate.

As liquid compositions for oral administration, emulsions which are pharmaceutically acceptable, solutions, suspensions, syrups and elixirs containing inert diluents such as water or liquid paraffin may be used. These compositions can also comprise substances other than diluents, e.g. wetting, sweetening or flavoring products.

The compositions for parenteral administration can be sterile solutions, aqueous or non-aqueous, suspensions or emulsions. As a solvent or vehicle, propylene glycol, a polyethylene glycol, vegetable oils, especially olive oil, and injectable organic esters, e.g. ethyl oleate, may be employed. These compositions can also contain adjuvants, especially wetting, emulsifying or dispersing agents. The sterilization may be carried out in several ways, e.g. using a bacteriological filter, by incorporating sterilizing agents in the composition, by irradiation or by heating. They can also be prepared in the form of sterile solid compositions which will be dissolved at the time of use in sterile water or any other sterile injectable medium.

The compositions for rectal administration are suppositories or rectal capsules, which can contain, apart from the active product, excipients such as cocoa butter or Suppocire.

In human or veterinary therapy, the compositions according to the invention are especially useful in the treatment of infections of bacterial origin.

Generally speaking, the doctor will determine the dosage he considers most suitable in accordance with the age, weight, degree of infection and other factors specific to the subject to be treated. Generally, the doses are between 0.2 and 1 of active product administered twice daily orally or parenterally for an adult.

The examples which follow, given without implied limitation, illustrate compositions according to the invention:

EXAMPLE A

Tablets containing a 250 mg dose of active product and having the following composition are prepared according to the usual techniques.

| | |
|---|---|
| (R)-7-fluoro-1-methyl-4-oxo-8-(3-phenyl-1-piperazinyl)-1,4-dihydrobenzo[b][1,8]-naphthyridine-3-carboxylic acid | 250 mg |
| starch | 50 mg |
| lactose | 35 mg |
| talc | 15 mg |

EXAMPLE B

Tablets containing a 250 mg dose of active product and having the following composition are prepared according to the usual techniques.

| | |
|---|---|
| (RS)-7-fluoro-8-[3-(2-furyl)-1-piperazinyl]-1-methyl-4-oxo-1,4-dihydrobenzo[b][1,8]naphthyridine-3-carboxylic acid | 250 mg |
| starch | 50 mg |
| lactose | 35 mg |
| talc | 15 mg |

The products of general formula (I) are also advantageous in the agrochemical field for antibacterial treatments of plants and vegetables. It is understood that the compositions for agrochemical use containing a product of general formula (I) also fall within the scope of the present invention.

Moreover, the products of general formula (I) may also be used as agents for the preservation or disinfection of organic or inorganic substances, in particular in the dyestuffs, fats, paper, wood or polymer industry or alternatively in the textile industry, the food industry or water treatment. It is also understood that the compositions containing a product of general formula (I), in the pure state or in the form of a combination with compatible diluents or adjuvants, also fall within the scope of the present invention.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A benzo[b][1,8]naphthyridine derivative of formula:

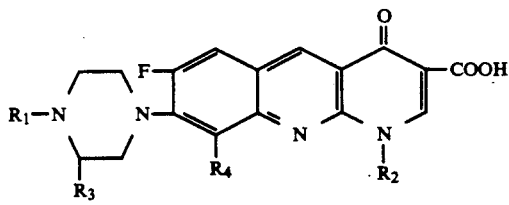

in which,
- $R_1$ represents a hydrogen atom or a hydroxyl or alkyl radical,
- $R_2$ represents a hydrogen atom or an alkyl or fluorolkyl radical, a cycloalkyl radical containing 3 to 6 carbon atoms or alkyloxy or alkylamino radical,
- $R_3$ represents a phenyl or phenylalkyl radical optionally substituted with at least one halogen atom or alkyl radical, cycloalkyl radical containing 3 to 6 carbon atoms, alkyloxy, cyano, amino, alkylamino, dialkylamino, alkyloxyalkyl, hydroxyalkyl, hydroxyalkyloxy, methylenedioxy, aminoalkyl or alkylaminoalkyl radicals or dialkylaminoalkyl radical in which the alkyl portions, with the nitrogen atom to which they are attached, can form a 5- or 6-membered heterocycle, or represents a 5-membered heterocyclic radical containing 1 or 2 hetero atoms selected from nitrogen, oxygen or sulphur, and
- $R_4$ represents a hydrogen atom or a fluorine atom, and in which the alkyl radicals are linear or branched and contain 1 to 4 carbon atoms, in its isomeric forms or mixtures thereof, as well as its metal salts, its addition salts with nitrogenous bases, its addition salts with acids and its hydrated forms.

2. A benzo[b][1,8]naphthyridine derivative according to claim 1, wherein:
- $R_1$ represents a hydrogen atom or a hydroxyl or alkyl radical,
- $R_2$ represents a hydrogen atom or an alkyl or fluoroalkyl radical, a cycloalkyl radical containing 3 to 6 carbon atoms or an alkyloxy radical,
- $R_3$ represents a phenyl or phenylalkyl radical optionally substituted with at least one halogen atom or alkyl radical, cycloalkyl radical containing 3 to 6 carbon atoms or alkyloxy, cyano, amino, alkyloxyalkyl, hydroxyalkyloxy or methylenedioxy radical, or represents a 5-membered heterocyclic radical containing 1 or 2 hetero atoms selected from nitrogen, oxygen or sulphur, and
- $R_4$ represents a hydrogen atom or a fluorine atom, and in which the alkyl radicals are linear or branched and contain 1 to 4 carbon atoms, in its isomeric forms or mixtures thereof, as well as its metal salts, its addition salts with nitrogenous bases, its addition salts with acids and it hydrated forms.

3. 7-Fluoro-1-methyl-4-oxo-8-(3-phenyl-1-piperazinyl)-1,4-dihydrobenzo[b][1,8]naphthyridine-3-carboxylic acid, in its isomeric forms or mixtures thereof as well as its metal salts, its addition salts with nitrogenous bases, its addition salts with acids and its hydrated forms.

4. 7-Fluoro-1-methyl-8-[3-(4-methylphenyl)-1-piperazinyl)-4-oxo-1,4-dihydrobenzo[b][1,8]naphthyridine-3-carboxylic acid, in its isomeric forms or mixtures thereof as well as its metal salts, its addition salts with nitrogenous bases, its addition salts with acids and its hydrated forms.

5. 7-Fluoro-8-[3-(4-methoxyphenyl)-1-piperazinyl)-1-methyl-4-oxo-1,4-dihydrobenzo[b][1,8]naphthyridine-3-carboxylic acid, in its isomeric forms or mixtures thereof as well as its metal salts, its addition salts with nitrogenous bases, its addition salts with acids and its hydrated forms.

6. 7,9-Difluoro-8-[3-(4-methoxyphenyl)-1-piperazinyl)-1-methyl-4-oxo-1,4-dihydrobenzo[b][1,8]naphthyridine-3-carboxylic acid, in its isomeric forms or mixtures thereof as well as its metal salts, its addition salts with nitrogenous bases, its addition salts with acids and its hydrated forms.

7. 7-Fluoro-8-[3-(2-furyl)-1-piperazinyl)-1-methyl-4-oxo-1,4-dihydrobenzo[b][1,8]naphthyridine-3-carboxylic acid, in its isomeric forms or mixtures thereof as well as its metal salts, its addition salts with nitrogenous bases, its addition salts with acids and its hydrated forms.

* * * * *